United States Patent
Holley

(10) Patent No.: US 11,717,214 B2
(45) Date of Patent: Aug. 8, 2023

(54) SCREENING, DIAGNOSIS AND MONITORING OF RESPIRATORY DISORDERS

(71) Applicant: ResMed Pty Ltd, Bella Vista (AU)

(72) Inventor: Liam Holley, Sydney (AU)

(73) Assignee: ResMed Pty Ltd

( * ) Notice: Subject to any disclaimer, the term of this patent is extended or adjusted under 35 U.S.C. 154(b) by 415 days.

(21) Appl. No.: 16/608,073

(22) PCT Filed: May 4, 2018

(86) PCT No.: PCT/AU2018/050409
§ 371 (c)(1),
(2) Date: Oct. 24, 2019

(87) PCT Pub. No.: WO2018/201197
PCT Pub. Date: Nov. 8, 2018

(65) Prior Publication Data
US 2020/0187852 A1    Jun. 18, 2020

(30) Foreign Application Priority Data

May 5, 2017 (AU) ................................. 2017901663
Nov. 13, 2017 (AU) ................................. 2017904590

(51) Int. Cl.
*A61B 5/00* (2006.01)
*A61B 5/08* (2006.01)
*A61B 7/00* (2006.01)

(52) U.S. Cl.
CPC .......... *A61B 5/4818* (2013.01); *A61B 5/7257* (2013.01); *A61B 7/003* (2013.01); *A61B 2562/0204* (2013.01)

(58) Field of Classification Search
CPC ..... A61B 5/4818; A61B 5/7257; A61B 7/003; A61B 2562/0204; A61B 5/08;
(Continued)

(56) References Cited

U.S. PATENT DOCUMENTS

| 4,944,310 A | 7/1990 | Sullivan |
| 5,195,528 A | 3/1993 | Hok |

(Continued)

FOREIGN PATENT DOCUMENTS

| CN | 101128150 A | 2/2008 |
| CN | 102596031 A | 7/2012 |

(Continued)

OTHER PUBLICATIONS

Edgar Cervantes, Kira: a ring light that will take your selfies to the next level, Jul. 21, 2015, Android Authority (Year: 2015).*

(Continued)

*Primary Examiner* — Etsub D Berhanu
(74) *Attorney, Agent, or Firm* — Botos Churchill IP Law LLP

(57) ABSTRACT

A system screens, diagnoses, or monitors sleep disordered breathing of a patient. The system may include a nasal cannula, a conduit connected to the nasal cannula at a first end, an adaptor configured to receive a second end of the conduit and/or a portable computing device. The adaptor may be configured to position the second end of the conduit in proximity with a microphone of the portable computing device. Optionally, a processor may generate an indicator to guide placement of the adaptor for use. Such positioning may, in use, permit the microphone to generate a patient breathing sound signal via the adaptor for processor(s) of the device. The processor(s) may then process the breathing sound signal. The process may include detecting SDB events from an extracted and/or de-rectified loudness signal. The process may include computing a metric of severity of a respiratory condition of the patient using detected SDB events.

16 Claims, 18 Drawing Sheets

(58) Field of Classification Search
CPC ... A61B 5/0803; A61B 5/0816; A61B 5/0826; A61B 5/4803
See application file for complete search history.

(56) References Cited

U.S. PATENT DOCUMENTS

| | | | |
|---|---|---|---|
| 5,245,995 | A | 9/1993 | Sullivan |
| 5,275,159 | A | 1/1994 | Griebel |
| 6,120,441 | A | 9/2000 | Griebel |
| 6,241,683 | B1 | 6/2001 | Macklem et al. |
| 6,532,959 | B1 | 3/2003 | Berthon-Jones |
| 9,801,590 | B2 | 10/2017 | Alshaer et al. |
| 2003/0130577 | A1* | 7/2003 | Purdy ............... A61M 25/0662 604/523 |
| 2006/0276718 | A1* | 12/2006 | Madaus ............... A61B 5/4818 600/538 |
| 2008/0319277 | A1* | 12/2008 | Bradley ............... A61B 7/003 600/301 |
| 2008/0319333 | A1* | 12/2008 | Gavish ............... A61B 7/003 600/529 |
| 2011/0313689 | A1* | 12/2011 | Holley ............... A61B 5/097 702/56 |
| 2012/0157794 | A1* | 6/2012 | Goodwin ........... A61B 5/14551 128/207.18 |
| 2013/0226020 | A1 | 8/2013 | Holley et al. |
| 2014/0188006 | A1* | 7/2014 | Alshaer ............... A61B 5/7475 600/586 |
| 2014/0200474 | A1* | 7/2014 | Selvaraj ............... A61B 5/0806 600/529 |
| 2015/0320960 | A1* | 11/2015 | Barlow ............ A61M 16/0683 128/205.25 |

FOREIGN PATENT DOCUMENTS

| | | | |
|---|---|---|---|
| WO | 2012058727 | A2 | 5/2012 |
| WO | WO-2013057637 | A1 * | 4/2013 ........... A61B 5/0826 |
| WO | 2017029317 | A1 | 2/2017 |
| WO | 2017132726 | A1 | 8/2017 |

OTHER PUBLICATIONS

International Search Report issued in corresponding PCT application No. PCT/AU2018/050409 dated Aug. 28, 2018.
Respiratory Physiology, by John B. West, Lippincott Williams & Wilkins, 9th edition published 2011.
Phonospirometry for noninvasive measurement of ventilation: methodology and preliminary results (J Appl. Physiol. 93: 1515-1526, Jun. 2002).
The First Office Action for Chinese Patent Application No. 2018800299541, dated Nov. 17, 2021.

* cited by examiner

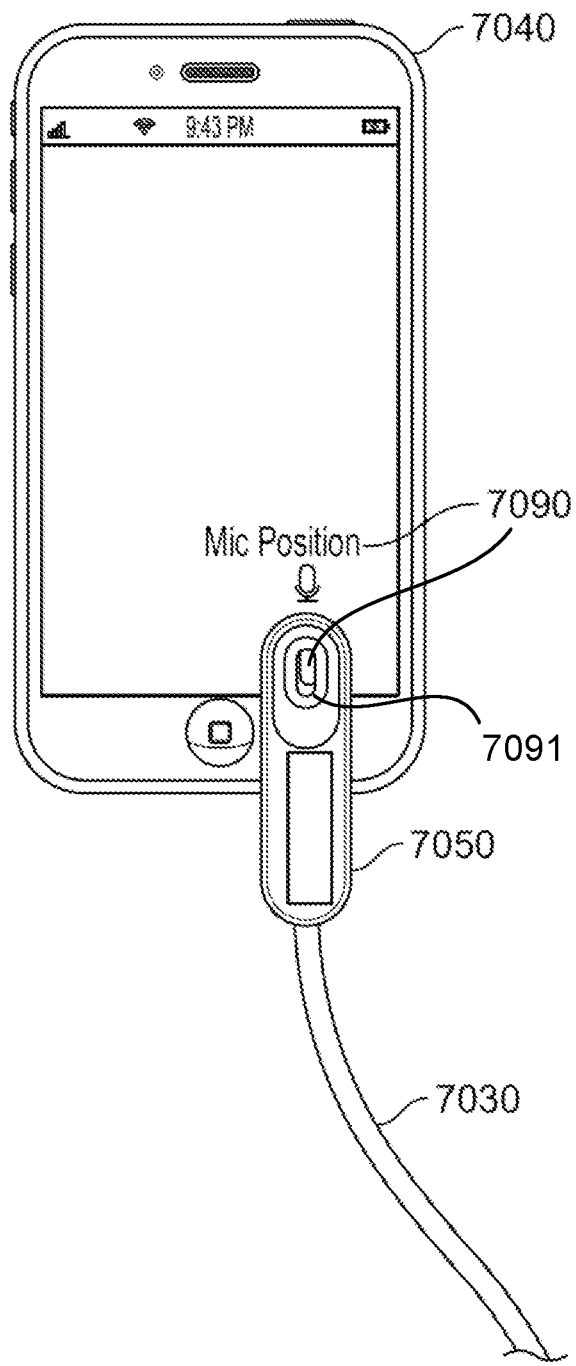
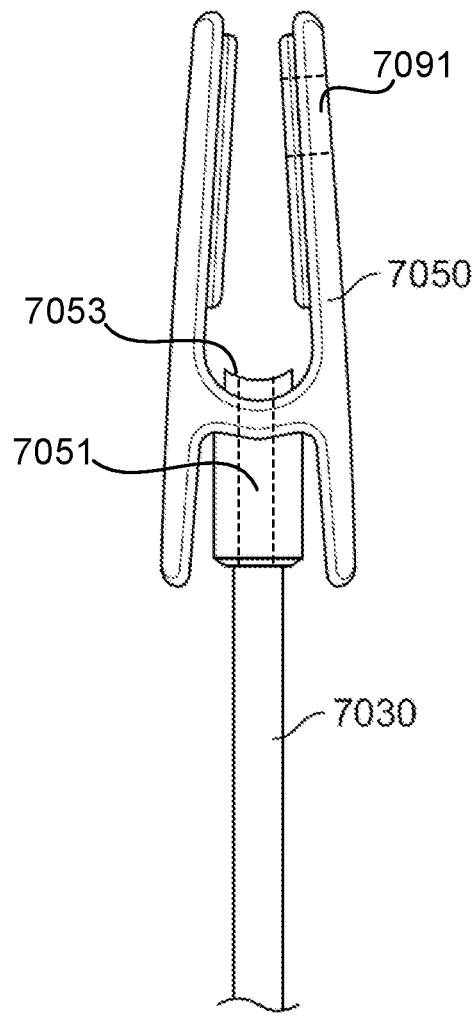
FIG. 7D
FIG. 7E

SCREENING, DIAGNOSIS AND MONITORING OF RESPIRATORY DISORDERS

1 CROSS-REFERENCE TO RELATED APPLICATIONS

The present application is a national phase entry under 35 U.S.C. § 371 of International Application No. PCT/AU2018/050409 filed May 4, 2018, published in English, which claims priority from Australian Provisional Patent Application No. 2017904590 filed Nov. 13, 2017 and Australian Provisional Patent Application No. 2017901663 filed May 5, 2017, all of which are incorporated herein by reference.

2 BACKGROUND OF THE TECHNOLOGY

2.1 Field of the Technology

The present technology relates to one or more of the screening, diagnosis, monitoring, treatment, prevention and amelioration of respiratory-related and other disorders. The present technology also relates to medical devices or apparatus, and their use for these purposes.

2.2 Description of the Related Art

2.2.1 Human Respiratory System and its Disorders

The respiratory system of the body facilitates gas exchange.

The nose and mouth form the entrances to the airways of a patient. The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Sleep Disordered Breathing comprises a wider spectrum of sleep-related breathing abnormalities than OSA. Milder forms of SDB include snoring and upper airway resistance syndrome (UARS).

Cheyne-Stokes respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

2.2.2 Therapy

A range of therapies have been used to treat or ameliorate SDB. Furthermore, otherwise healthy individuals may take advantage of such therapies to prevent respiratory disorders from arising.

Continuous Positive Airway Pressure (CPAP) therapy is a respiratory pressure therapy that has been used to treat OSA and UARS. The mechanism of action is that continuous positive airway pressure acts as a pneumatic splint and reduces upper airway obstruction by pushing the soft palate and tongue forward and away from the posterior oropharyngeal wall.

2.2.3 Treatment Systems

CPAP therapy may be provided by a treatment system or device. A treatment system may comprise a Respiratory Pressure Therapy Device (RPT device), an air circuit, a humidifier, and a patient interface, and data management, as illustrated in FIG. 1.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above. One known RPT device used for treating sleep disordered breathing is the S9 Sleep Therapy System, manufactured by ResMed Limited.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

2.2.3.4 Data Management

There may be clinical reasons to obtain data to determine whether the patient prescribed with respiratory therapy has been "compliant", e.g. that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

2.2.4 Screening, Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a person in order to record various bodily signals such as electroencephalography (EEG), electrocardiography (ECG), electrooculograpy (EOG), electromyography (EMG), etc. PSG as a precursor to treatment for sleep disordered breathing has traditionally involved two nights of observation of a patient in a clinic, one night of pure diagnosis and a second night of titration of treatment parameters by a clinician. In particular, for these reasons, PSG is unsuitably expensive and inconvenient for home screening/diagnosis/monitoring of sleep disordered breathing.

A need therefore exists for a more convenient, less expensive, system for screening/diagnosis/monitoring of sleep disordered breathing.

3 BRIEF SUMMARY OF THE TECHNOLOGY

The present technology is directed towards providing medical devices used in the screening, diagnosis, or monitoring of respiratory disorders having one or more of improved comfort, cost, efficacy, ease of use, and manufacturability.

A first aspect of the present technology relates to systems and methods used in the screening, diagnosis, or monitoring of a respiratory disorder.

The present technology utilises an apparatus configured to communicate biological sounds (biosounds) such as breathing to the microphone of a commonly available portable programmable computing device, which is configured to analyse the sounds to screen/diagnose/monitor SDB or other disorders.

Some versions of the present technology may include apparatus including a nasal cannula. The apparatus may include a conduit connected to the nasal cannula at a first end. The apparatus may include an adaptor configured to receive a second end of the conduit and a portable computing device to position the second end of the conduit in proximity with a microphone of the portable computing device.

In some versions, the adaptor may be a cradle. In some versions, the adaptor may be a clip. The nasal cannula may include one or two projections that are configured in use to be inserted non-invasively a little way into respective nares of a patient. Optionally, at least one of the one or two projections may be configured to partially impede the patient's respiration so as to increase an amount of turbulence of respired air around an entrance to the nares. The apparatus may include an acoustic resonator in the conduit. The adaptor may be configured with a channel to provide an acoustic path through the adaptor to a microphone opening of a housing of the portable computing device. The channel of the adaptor may be configured for direct alignment with the microphone opening when the adaptor is applied to the housing of the portable computing device. Optionally, the adaptor may include a coupling edge configured to at least partially surround a microphone opening of a housing of the portable computing device. The adaptor may include a sleeve portion configured to generally conform about a perimeter of an end housing portion of the portable computing device.

Some versions of the present technology may include a method of one or more processors to screen, diagnose, or monitor sleep disordered breathing (SDB) of a patient. The method may include extracting a loudness signal from a breathing sound signal of the patient generated by a microphone. The method may include de-rectifying the loudness signal. The method may include detecting SDB events in the de-rectified loudness signal. The method may include computing a metric of severity of SDB of the patient from the detected SDB events.

In some versions, the method may include generating an output based on the metric of severity. Generating the output may include comparing the metric of severity with a severity threshold. Extracting the loudness signal from the breathing sound signal may include low-pass filtering a root mean square (RMS) value of a window that slides over the breathing sound signal. Extracting the loudness signal from the breathing sound signal may include filtering the breathing sound signal to limit included frequencies to a portion of an audio frequency range. Extracting the loudness signal from the breathing sound signal may include summing magnitudes of Fourier transform values of the breathing sound signal within a portion of an audio frequency range. Extracting the loudness signal from the breathing sound signal may include calculating a power in a resonant frequency range of a window that slides over the breathing sound signal. Extracting the loudness signal from the breathing sound signal may include detecting frequency modulation around a basic resonant frequency.

In some versions, the method may include filtering the loudness signal to permit an upper frequency that is at two times an upper frequency limit of a human breathing frequency range. The SDB events may be one or more of: apneas; hypopneas; periods of Cheyne-Stokes respiration; snores; and flow limitations. The method may include computing a measure of quality of the loudness signal. Computing a measure of quality may include determining whether the loudness signal has most of its power in a human breathing frequency range. De-rectifying the loudness signal may include identifying peaks of the loudness signal and determining which peaks correspond to expiratory portions of a breathing cycle. De-rectifying the loudness signal may include identifying peaks of the loudness signal and determining which peaks correspond to inspiratory portions of a breathing cycle. The identifying may be based on a duration of a period between at least two successive peaks of the loudness signal. Optionally, when the duration is determined to be shorter than a threshold, (a) an initial peak of the at least two successive peaks may be identified as an inspiratory peak, or (b) a following peak of the at least two successive peaks may be identified as an expiratory peak. The threshold may include a duration of another period between successive peaks, and wherein the another period precedes or follows the period. The identifying may be based on a shape of the peaks of the loudness signal, wherein an expiratory peak may be more exponentially decaying than an inspiratory peak. The identifying may be based on frequency content of the peaks of the loudness signal.

In some versions, the method may include generating a clip location indicator on a display coupled to the one or more processors. The clip location indicator may indicate a location on the display where attachment of a clip permits alignment between a channel of the clip and the microphone.

Some versions of the present technology may include a processor-readable medium. The processor-readable medium may have stored thereon processor-executable instructions which, when executed by a processor of a portable computing device, cause the processor to screen, diagnose, or monitor sleep disordered breathing (SDB) of a patient. The processor-executable instructions may be configured to execute any of methods described herein.

Some versions of the present technology may include a portable computing device. The portable computing device may include such a processor-readable medium. The portable computing device may include a microphone, a display and one or more processors configured to access the processor-readable medium to execute the processor-executable instructions of the the processor-readable medium to screen, diagnose, or monitor sleep disordered breathing (SDB) of a patient.

Some versions of the present technology may include a server with access to such a processor-readable medium. The server may be configured to receive requests for downloading the processor-executable instructions of the processor-readable medium to a portable computer device over a network.

Some versions of the present technology may include a method of a server having access to such a processor-readable medium. The method may include receiving, at the server, a request for downloading the processor-executable instructions of the processor-readable medium to a portable computer device over a network. The method may include transmitting the processor-executable instructions to the portable computer device in response to the request.

Some versions of the present technology may include a system for screening, diagnosing, or monitoring sleep disordered breathing (SDB) of a patient. The system may include a nasal cannula. The system may include a conduit connected to the nasal cannula at a first end. The system may include an adaptor configured to receive a second end of the conduit and a portable computing device to position the second end of the conduit in proximity with a microphone of the portable computing device such that, in use, the microphone generates a breathing sound signal of the patient. The system may include a processor configured to compute a metric of severity of the patient's SDB from the breathing sound signal.

In some versions, the processor may be a processor of the portable computing device. The processor may be a processor of a remote computing device with which the portable computing device is in communication. The adaptor may be a cradle or a clip. The processor may be configured to generate a clip location indicator on a display coupled to the processor. The clip location indicator may indicate a location on the display where attachment of a clip permits alignment between a channel of the clip and the microphone. The adaptor may be configured with a channel to provide an acoustic path through the adaptor to a microphone opening of a housing of the portable computing device. The channel of the adaptor may be configured for direct alignment with the microphone opening when the adaptor is applied to the housing of the portable computing device. The adaptor may include a coupling edge configured to at least partially surround a microphone opening of a housing of the portable computing device. The adaptor may include a sleeve portion configured to generally conform about a perimeter of an end housing portion of the portable computing device. The system may include an acoustic resonator located in the conduit.

Some versions of the present technology may include apparatus including means for generating a breathing sound signal of a patient. The apparatus may include means for extracting a loudness signal from the breathing sound signal. The apparatus may include means for de-rectifying the loudness signal. The apparatus may include means for detecting sleep disordered breathing (SDB) events in the loudness signal. The apparatus may include means for computing a metric of severity of the patient's SDB from the detected SDB events.

Some versions of the present technology may include a method of one or more processors to estimate a respiratory flow rate signal from a breathing sound signal of a patient. The method may include extracting a loudness signal from the breathing sound signal generated by a microphone. The method may include de-rectifying the loudness signal to estimate the respiratory flow rate signal of the patient.

In some versions, extracting the loudness signal from the breathing sound signal may include low-pass filtering a root mean square (RMS) value of a window that slides over the breathing sound signal. Extracting the loudness signal from the breathing sound signal may include filtering the breathing sound signal to limit included frequencies to a portion of an audio frequency range. Extracting the loudness signal from the breathing sound signal may include summing magnitudes of Fourier transform values of the breathing sound signal within a portion of an audio frequency range. Extracting the loudness signal from the breathing sound signal may include calculating a power in a resonant frequency range of a window that slides over the breathing sound signal. Extracting the loudness signal from the breathing sound signal may include detecting frequency modulation around a basic resonant frequency. The method may include filtering the loudness signal to permit an upper frequency that is at two times an upper limit of a human breathing frequency range. De-rectifying the loudness signal may include identifying peaks of the loudness signal and determining which peaks correspond to expiratory portions of a breathing cycle. De-rectifying the loudness signal may include identifying peaks of the loudness signal and determining which peaks correspond to inspiratory portions of a breathing. The identifying may be based on a duration of a period between at least two successive peaks of the loudness signal. In some versions, when the duration is determined to be shorter than a threshold, (a) an initial peak of the at least two successive peaks may be identified as an inspiratory peak or (b) a following peak of the at least two successive peaks may be identified as an expiratory peak. The threshold may include a duration of another period between successive peaks, and the another period may precede or follow the period. The identifying may be based on a shape of the peaks of the loudness signal, wherein an expiratory peak is more exponentially decaying than an inspiratory peak. The identifying may be based on frequency content of the peaks of the loudness signal. The method may include generating a clip location indicator on a display coupled to the one or more processors, wherein the clip location indicator indicates a location on the display where attachment of a clip permits alignment between a channel of the clip and the microphone.

Some versions of the present technology may include apparatus include means for extracting a loudness signal from a breathing sound signal of a patient. The apparatus may include means for de-rectifying the loudness signal to estimate a respiratory flow rate signal of the patient. In some versions, the apparatus may include means for conducting breathing sounds from nares of the patient to a microphone of a portable computing device.

According to one aspect of the present technology, there is provided apparatus comprising a nasal cannula; a conduit connected to the nasal cannula at a first end; and an adaptor configured to receive a second end of the conduit and a portable computing device such that the second end of the conduit is brought into proximity with a microphone of the portable computing device.

According to one aspect of the present technology, there is provided a method of screening, diagnosis, or monitoring sleep disordered breathing of a patient. The method comprises extracting a loudness signal from a breathing sound signal of the patient; detecting SDB events in the loudness signal; and computing a metric of severity of a respiratory condition of the patient using the detected SDB events.

According to a further aspect of the present technology there is provided a system for screening, diagnosing, or monitoring sleep disordered breathing of a patient. The system comprises: a nasal cannula; a conduit connected to the nasal cannula at a first end; an adaptor configured to receive a second end of the conduit and a portable computing device such that the second end of the conduit is brought into proximity with a microphone of the portable computing device such that, in use, the microphone generates a breathing sound signal of the patient; and a processor configured to carry out an analysis method. The method comprises extracting a loudness signal from the breathing sound signal; detecting SDB events in the loudness signal; and computing a metric of severity of a respiratory condition of the patient using the detected SDB events.

According to a further aspect of the present technology there is provided apparatus comprising means for generating a breathing sound signal of a patient, means for extracting a loudness signal from the breathing sound signal, means for detecting SDB events in the loudness signal, and means for computing a metric of severity of a respiratory condition of the patient using the detected SDB events.

According to a further aspect of the present technology there is provided a method of estimating a respiratory flow rate signal from a breathing sound signal of a patient. The method comprises extracting a loudness signal from the breathing sound signal; and de-rectifying the loudness signal to estimate the respiratory flow rate signal of the patient.

According to a further aspect of the present technology there is provided apparatus comprising means for extracting a loudness signal from a breathing sound signal of a patient; and means for de-rectifying the loudness signal to estimate a respiratory flow rate signal of the patient.

The methods/systems/devices/apparatus described herein can provide improved functioning in a processor, such as of a processor of a specific purpose computer, respiratory monitor and/or a respiratory therapy apparatus. Moreover, the methods/devices/apparatus can provide improvements in the technological field of automated screening, diagnosis, monitoring and/or treatment of respiratory disorders, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Breathing Waveforms

4.4 Screening/Diagnosis/Monitoring Systems and Methods

Figure 7A:
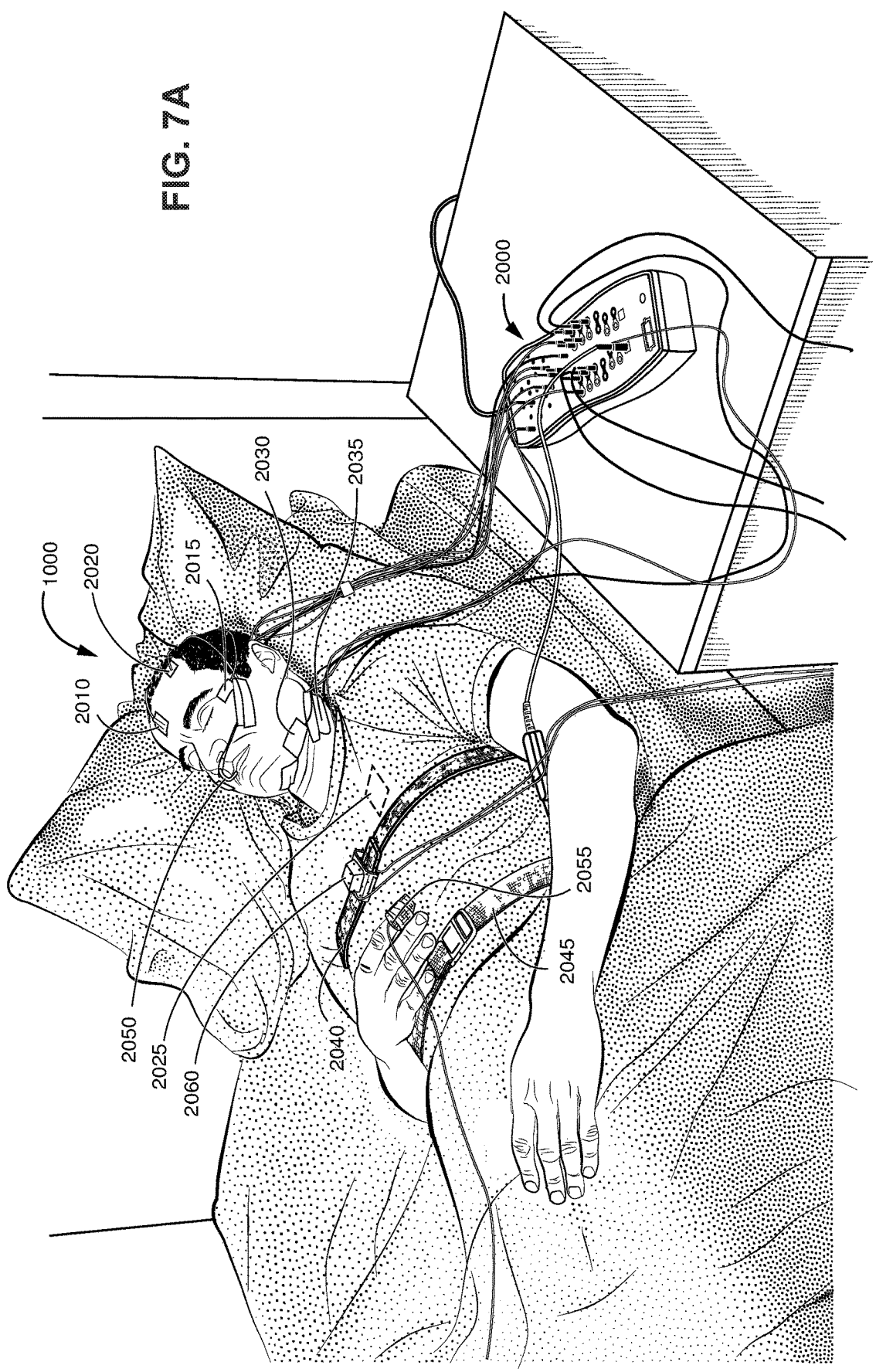

FIG. 7A shows a patient 1000 undergoing polysomnography.

Figure 7B:
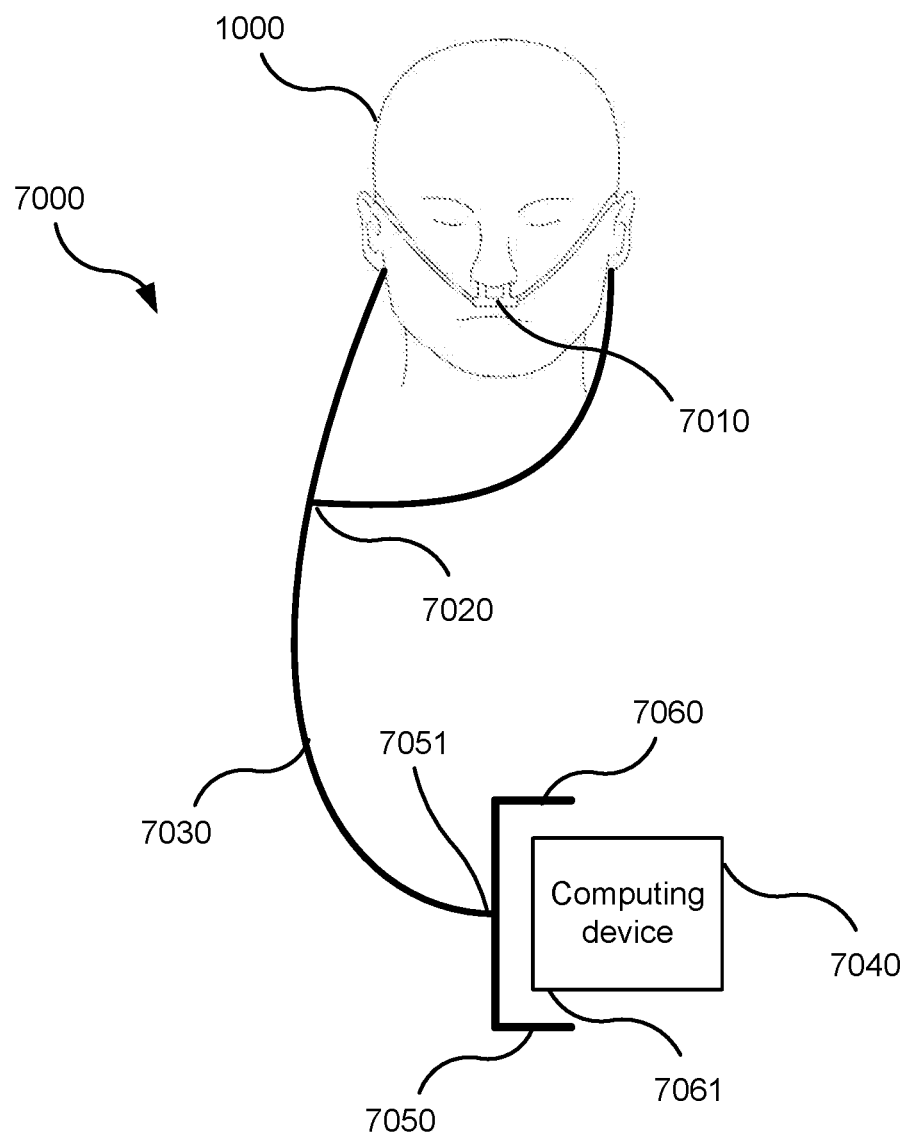

FIG. 7B is a schematic representation of a system for screening, diagnosing, or monitoring SDB according to one form of the present technology.

Figure 7C:
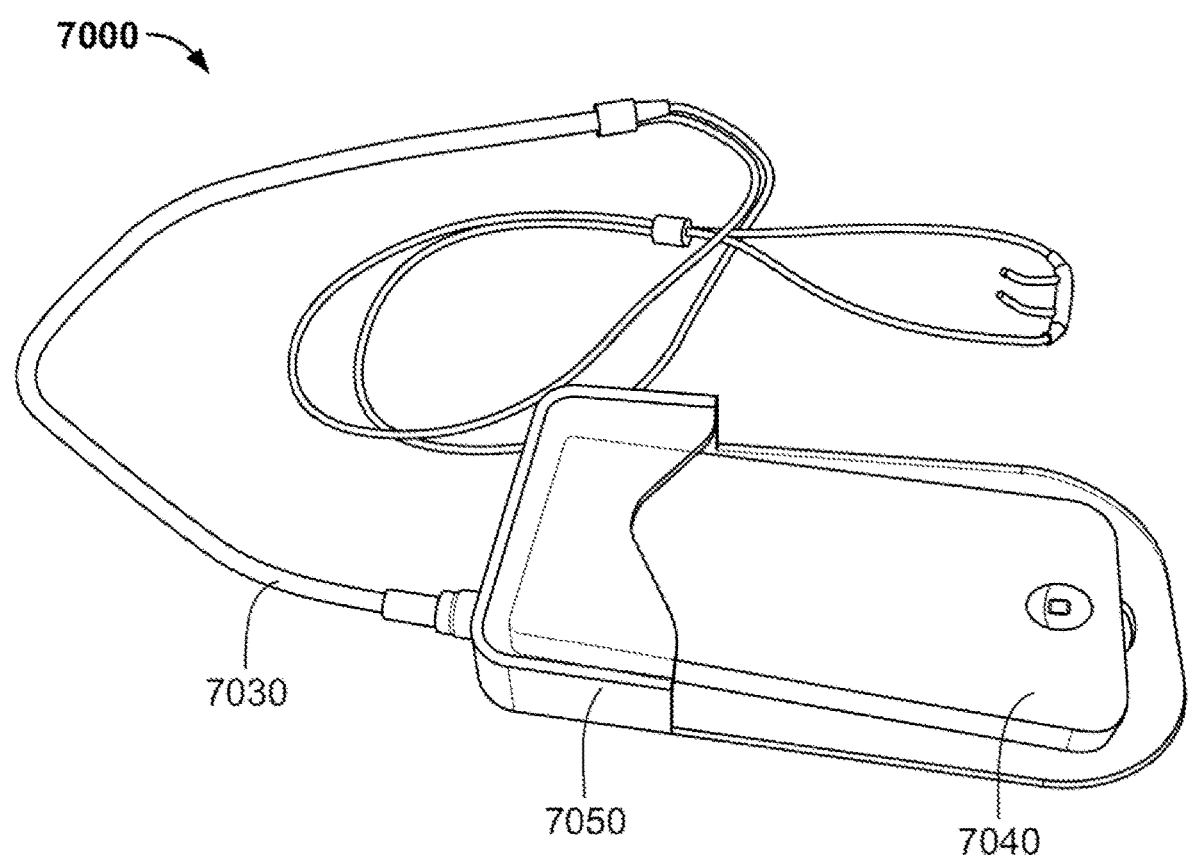

FIG. 7C is an illustration of one implementation of a screening/diagnosis/monitoring system of FIG. 7B comprising an adaptor in the form of a cradle, a portable computing device, and a conduit.

FIG. 7D is an illustration of another implementation of a screening/diagnosis/monitoring system of FIG. 7B comprising an adaptor in the form of a clip, a portable computing device, and a conduit.

FIG. 7E is a side view of the clip and the conduit of FIG. 7D.

Figure 7F:
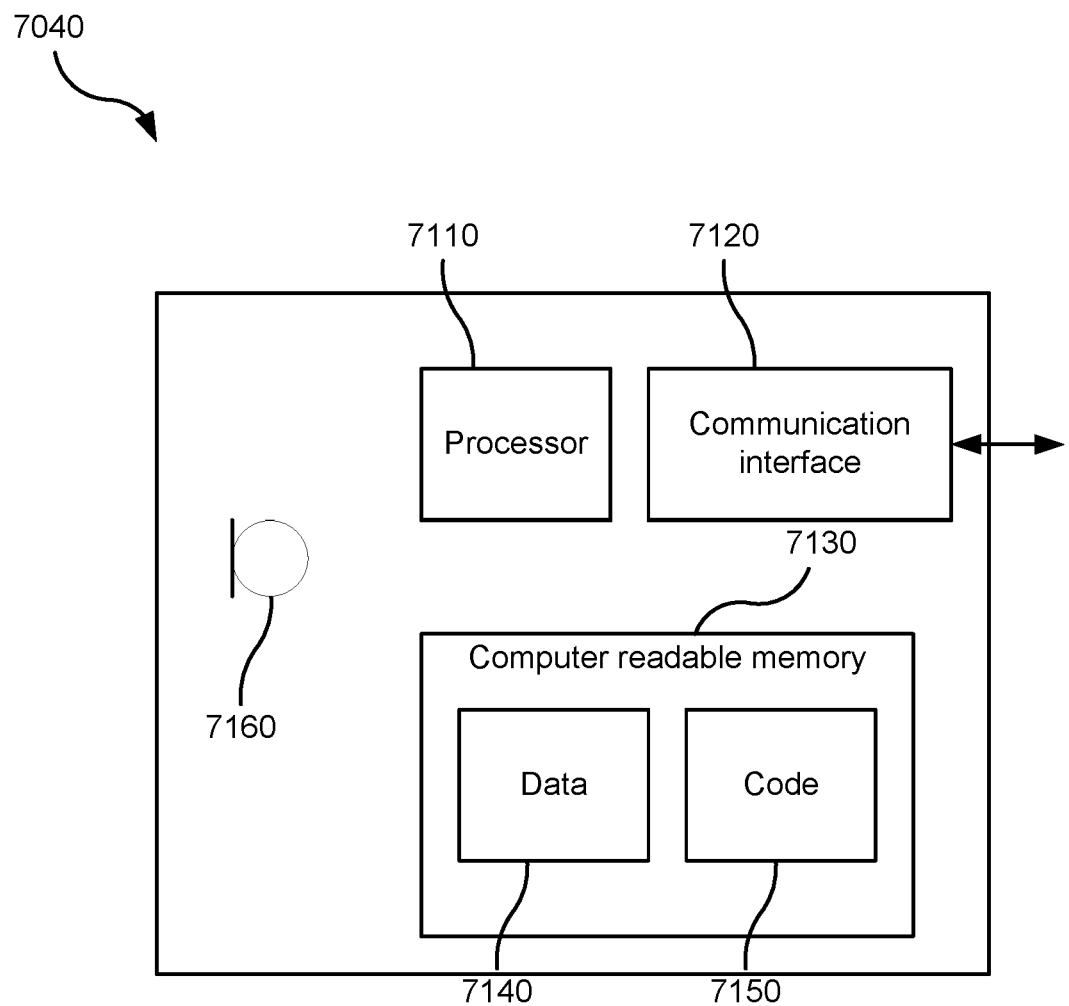

FIG. 7F is a block diagram illustrating the portable computing device of the screening/diagnosis/monitoring system of FIG. 7B in greater detail.

Figure 7G:
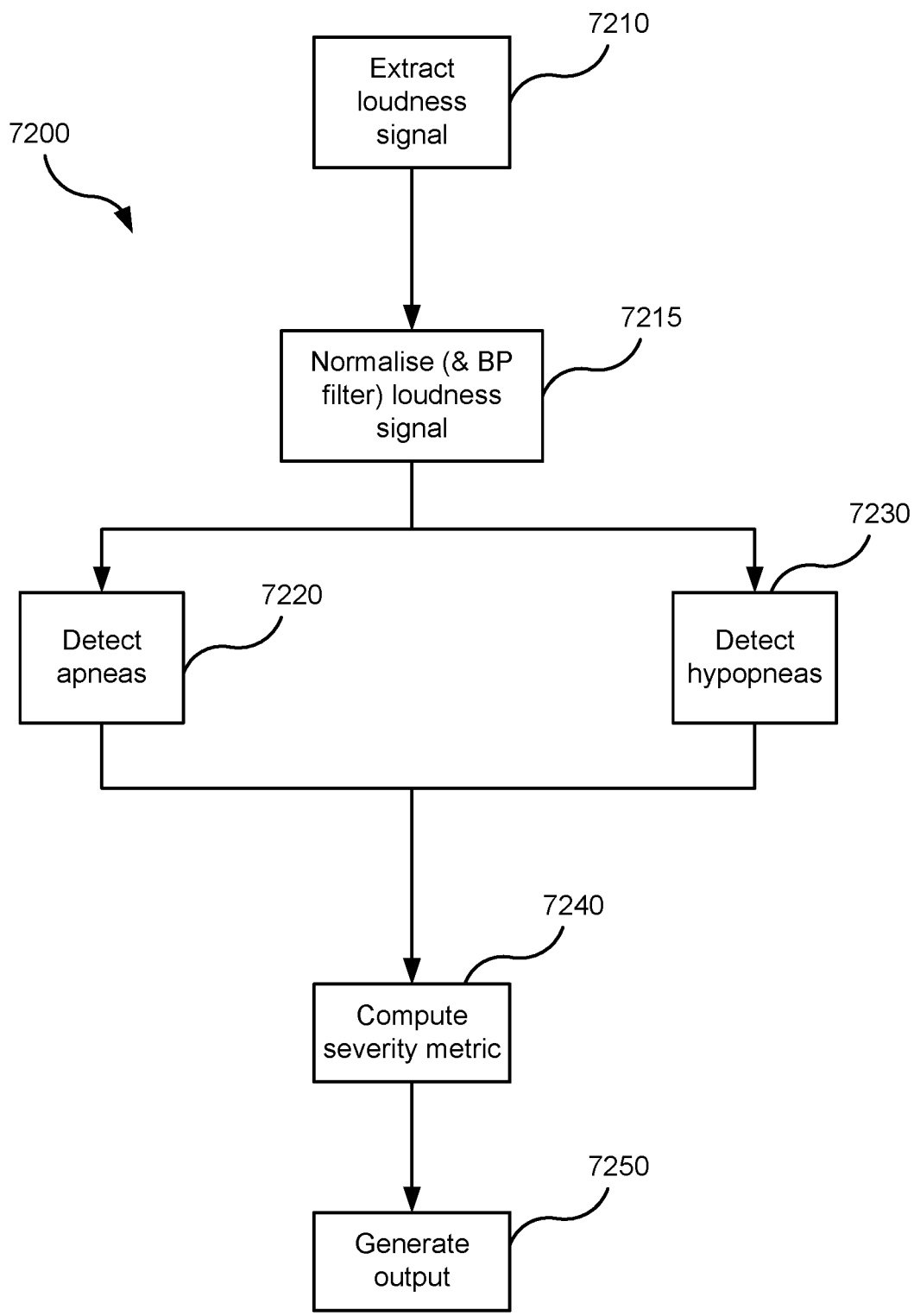

FIG. 7G is a flow chart illustrating a method of screening, diagnosis, or monitoring of SDB using the system of FIG. 7B according to one form of the present technology.

Figure 7H:
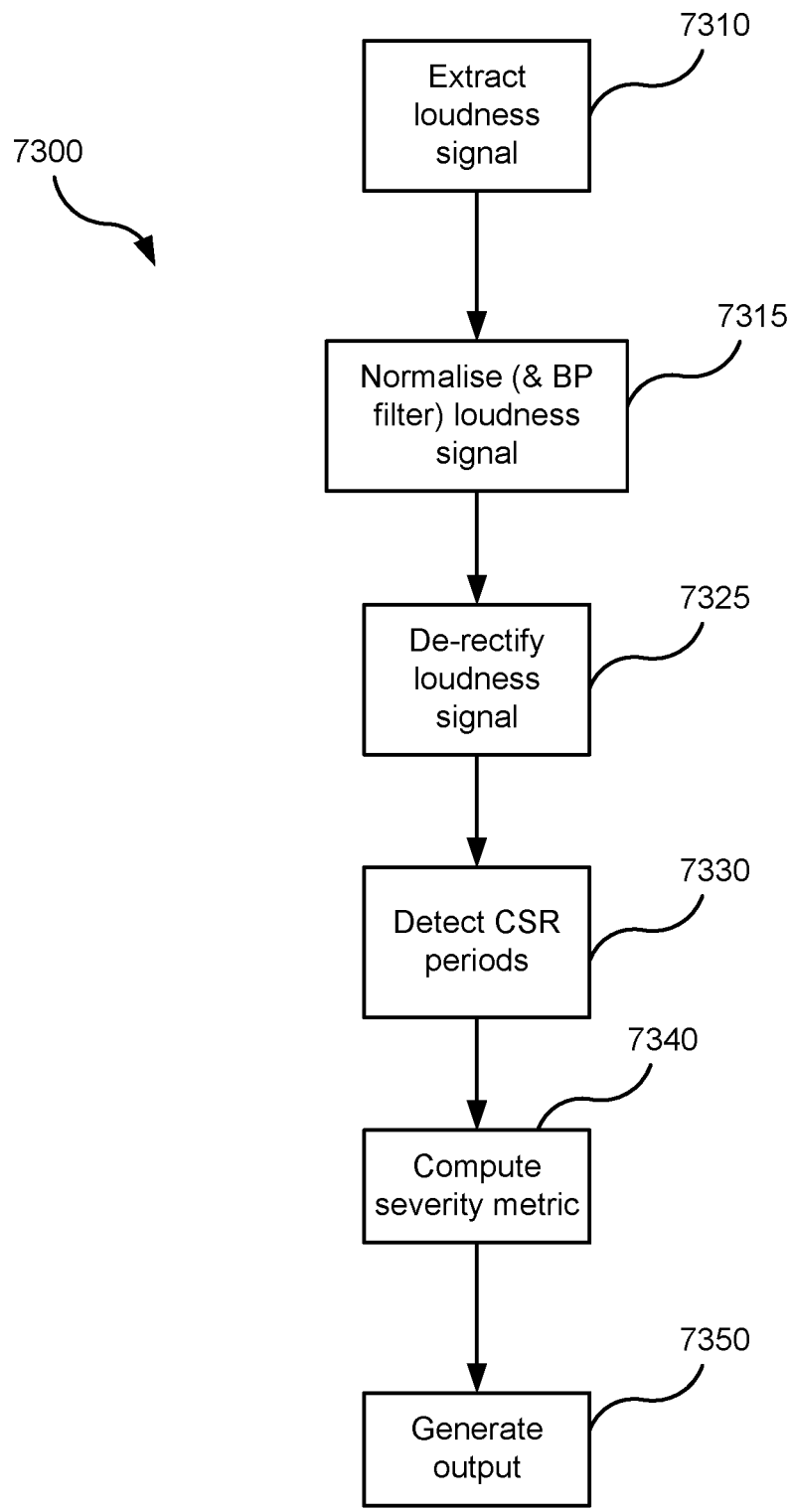

FIG. 7H is a flow chart illustrating a method of screening, diagnosis, or monitoring of SDB using the system of FIG. 7B according to another form of the present technology.

Figure 8A:
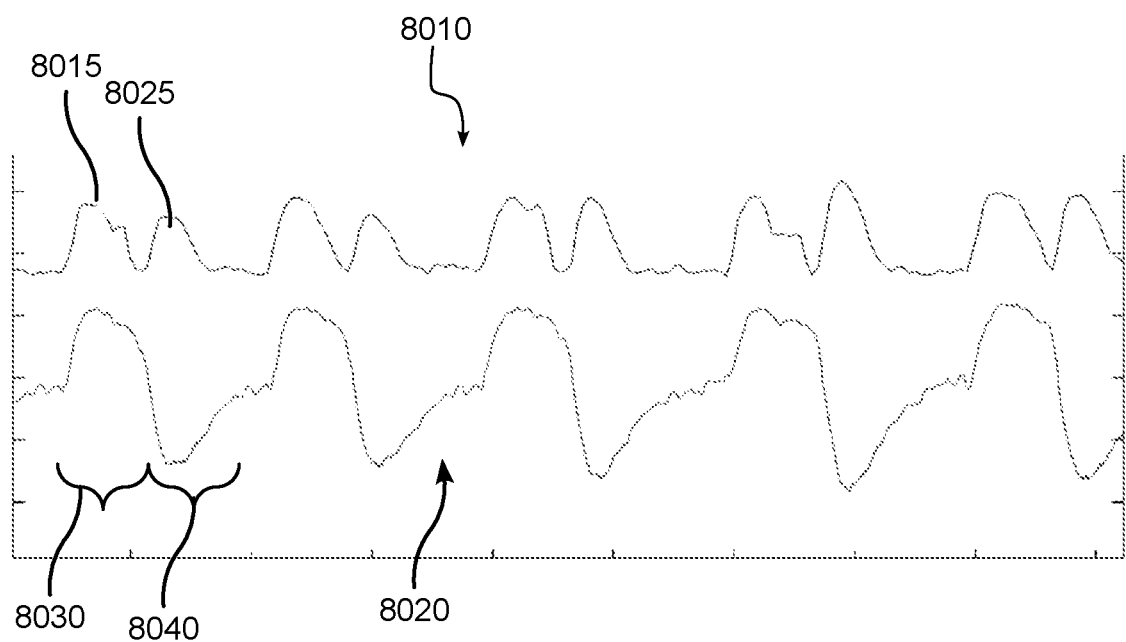

FIG. 8A contains a graph illustrating the similarity of the loudness of a breathing sound signal to a respiratory flow rate signal.

Figure 8B:
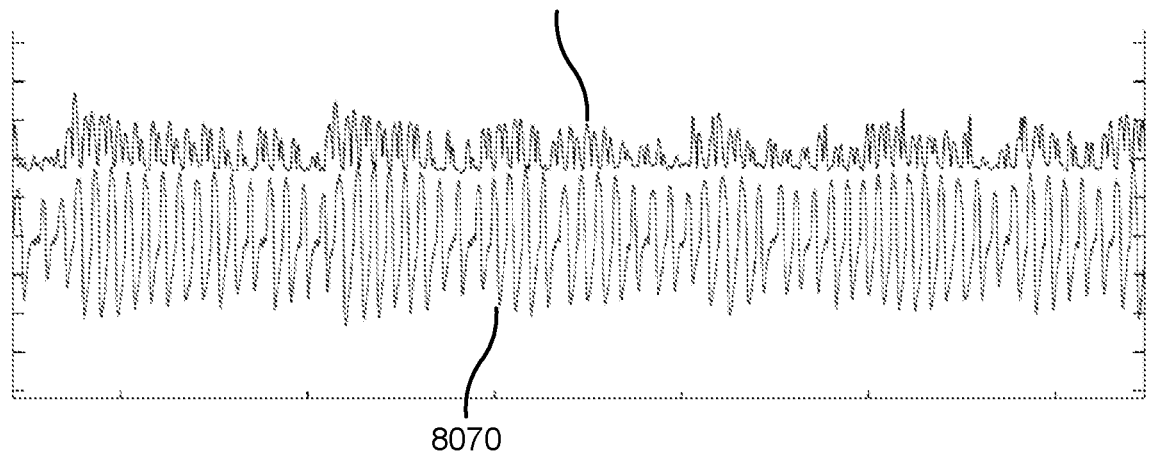

FIG. 8B contains a graph further illustrating the similarity of the loudness of a breathing sound signal to a respiratory flow rate signal.

Figure 8C:
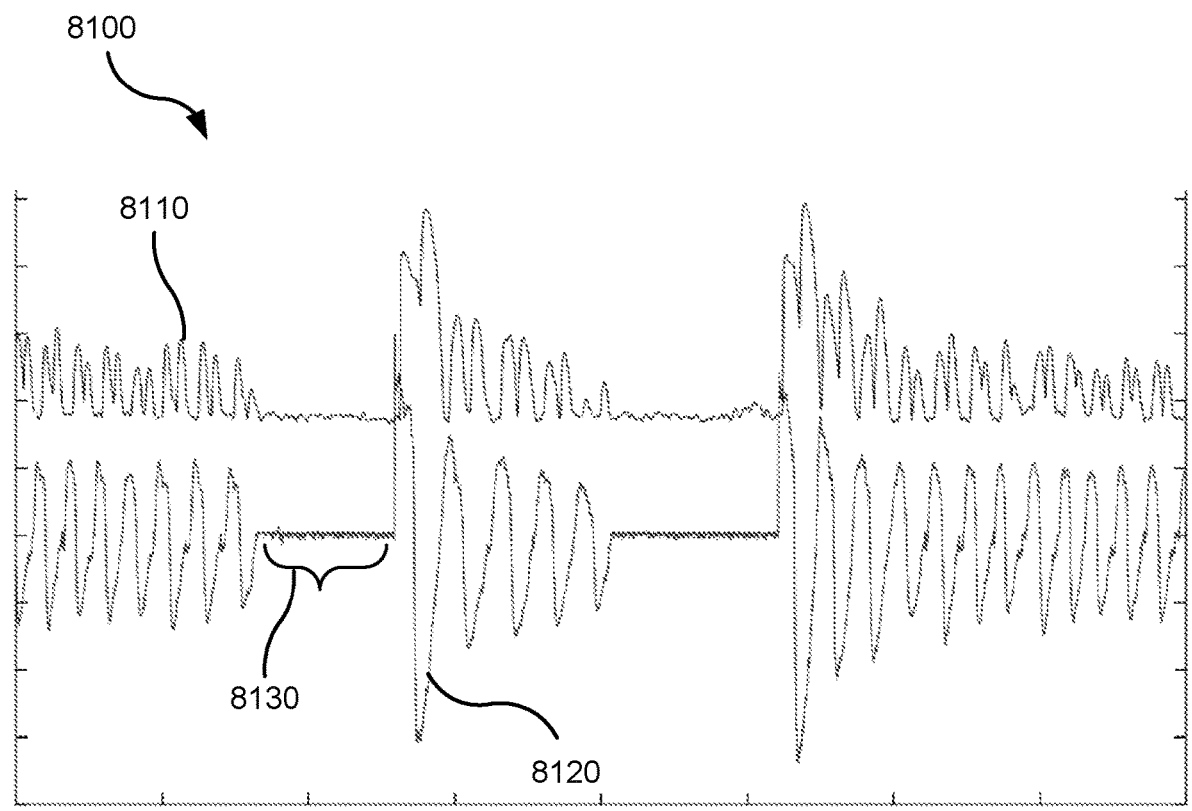

FIG. 8C contains a graph further illustrating the similarity of the loudness of a breathing sound signal to a respiratory flow rate signal.

Figure 9B:
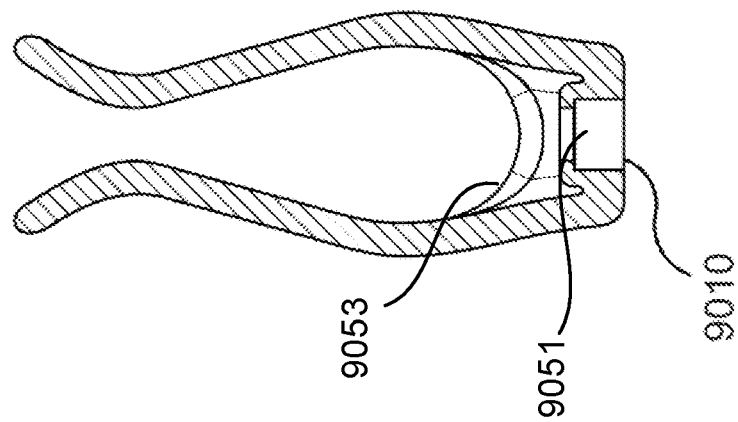
Figure 9A:
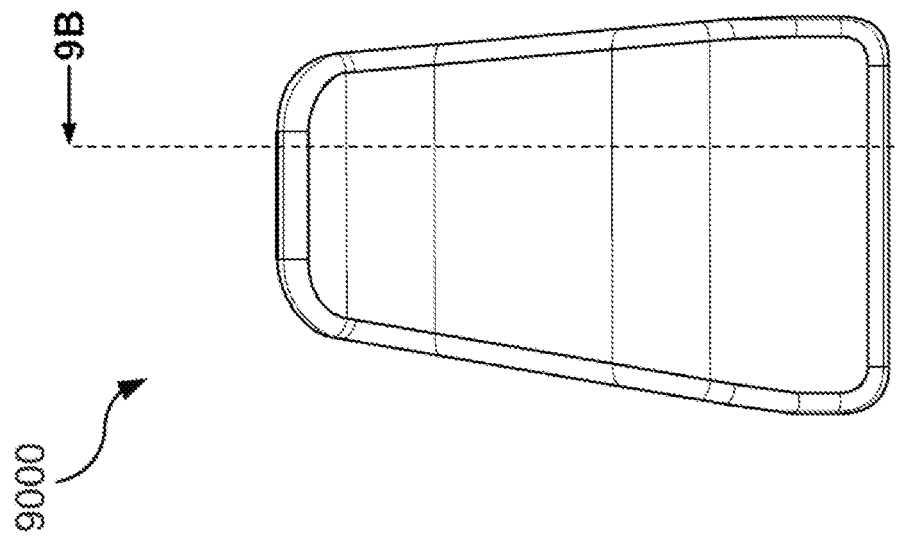

FIG. 9A is a plan view of an alternative implementation of the adaptor of FIG. 7B in the form of a clip.

FIG. 9B is a cross-sectional view of the clip of FIG. 9A.

Figure 10:
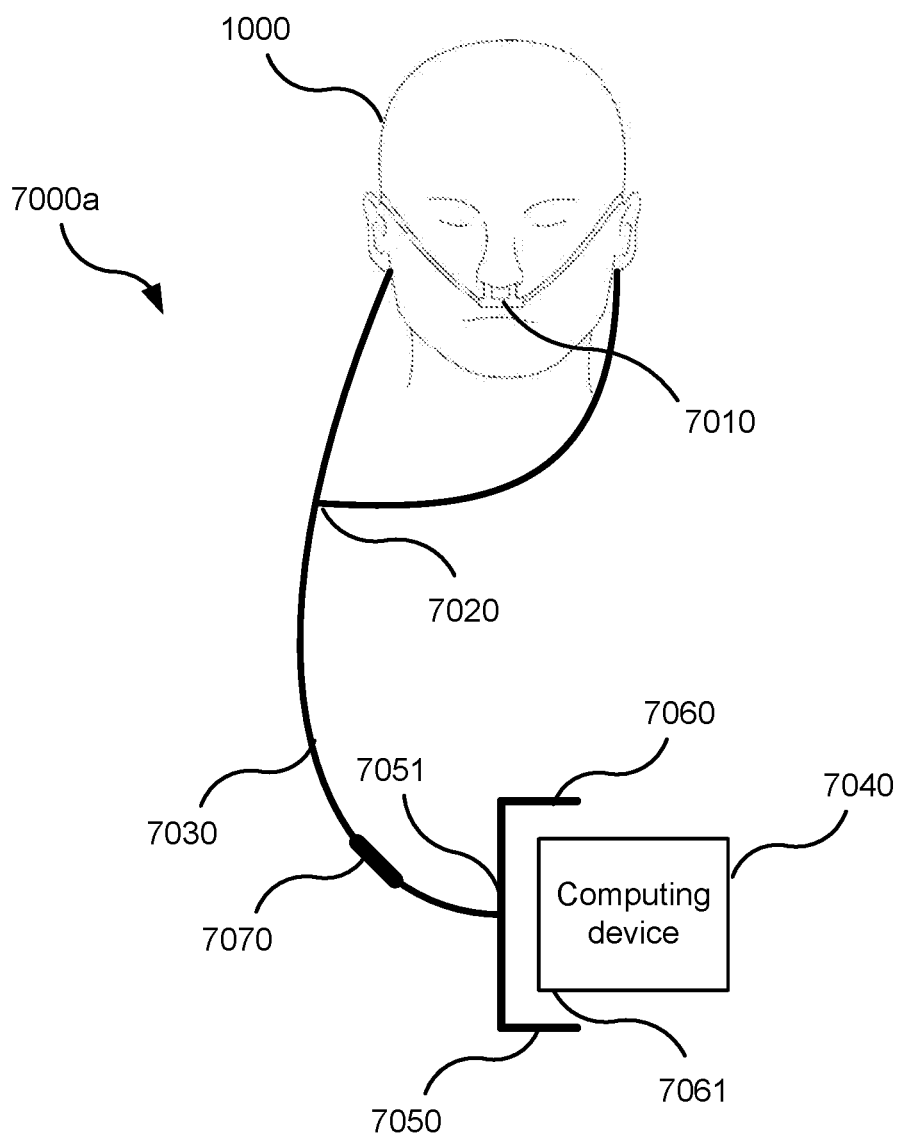

FIG. 10 is a schematic representation of a system for screening, diagnosing, or monitoring SDB according to an alternative form of the present technology

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Breathing Waveforms

Figure 1:
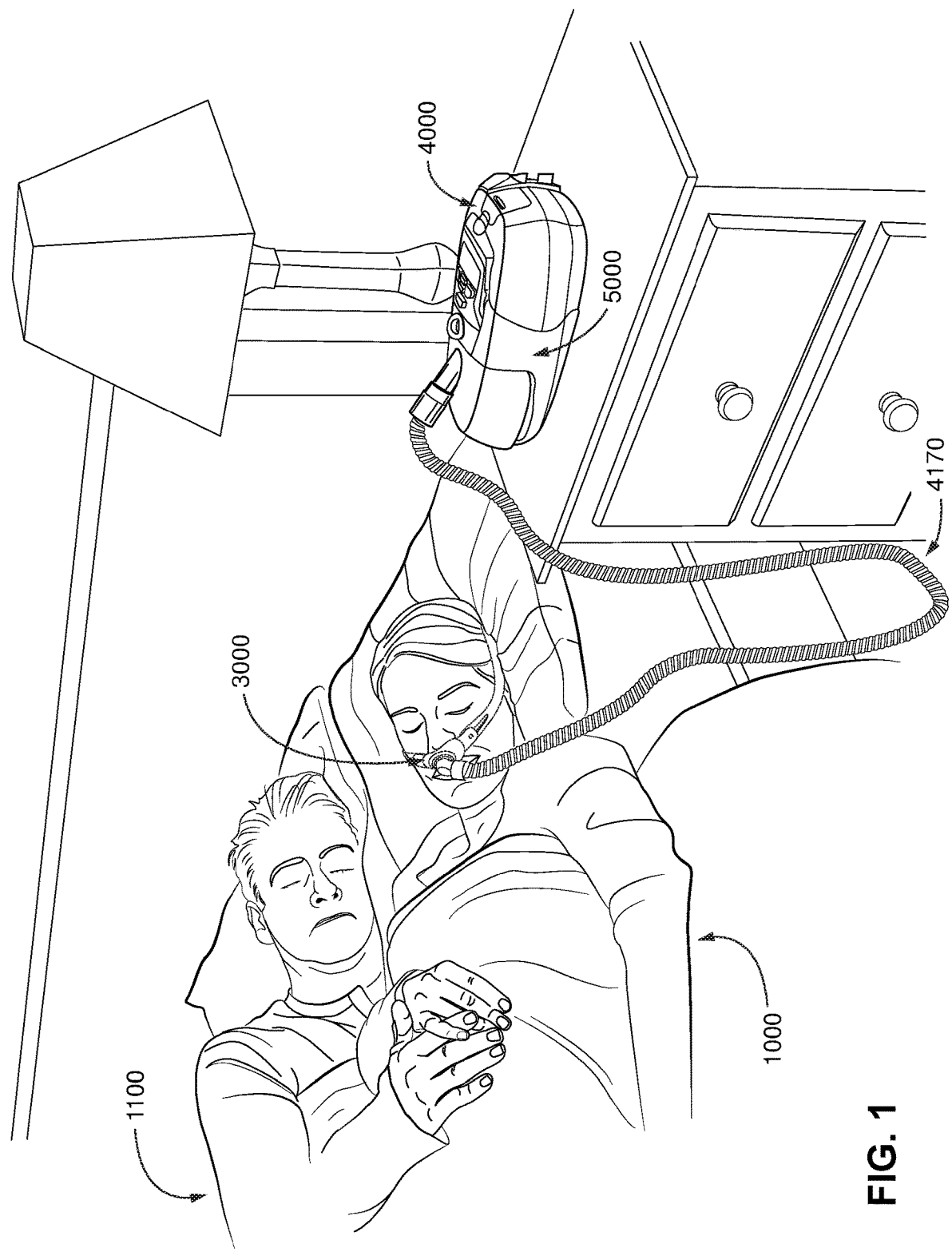
Figure 2:
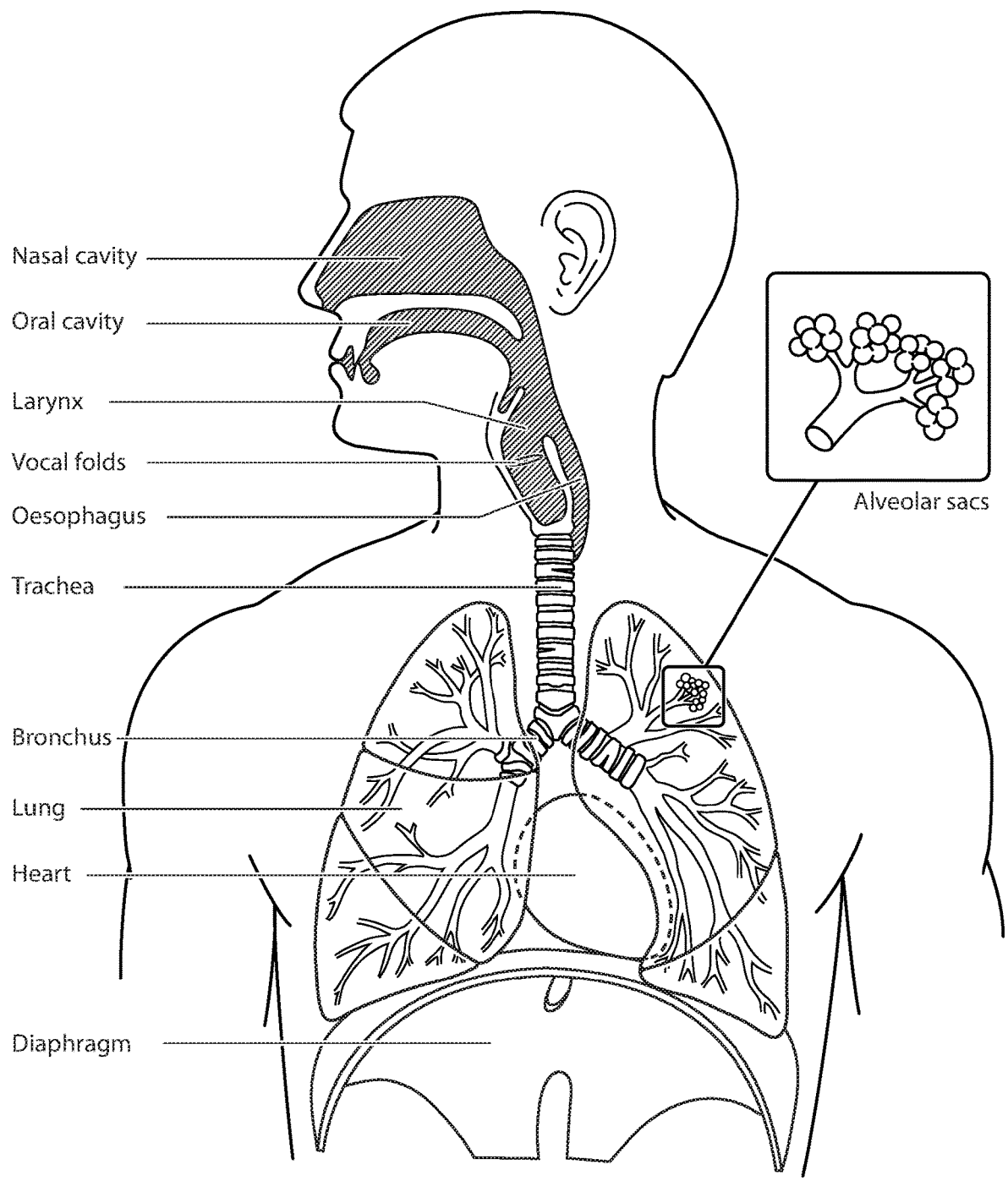
Figure 3:
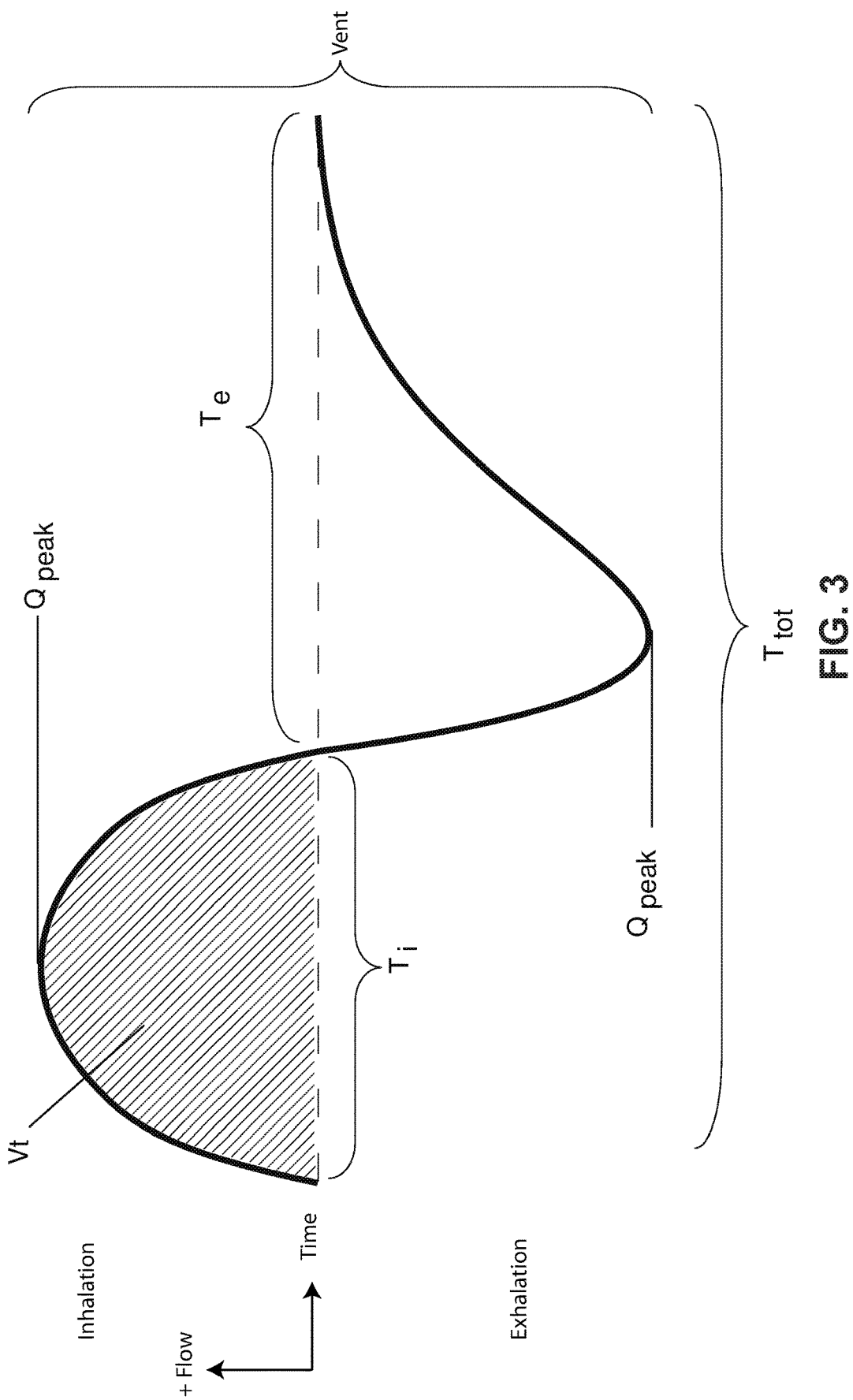
FIG. 3 shows a model typical breath waveform of a person while sleeping.

FIG. 3 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 4:
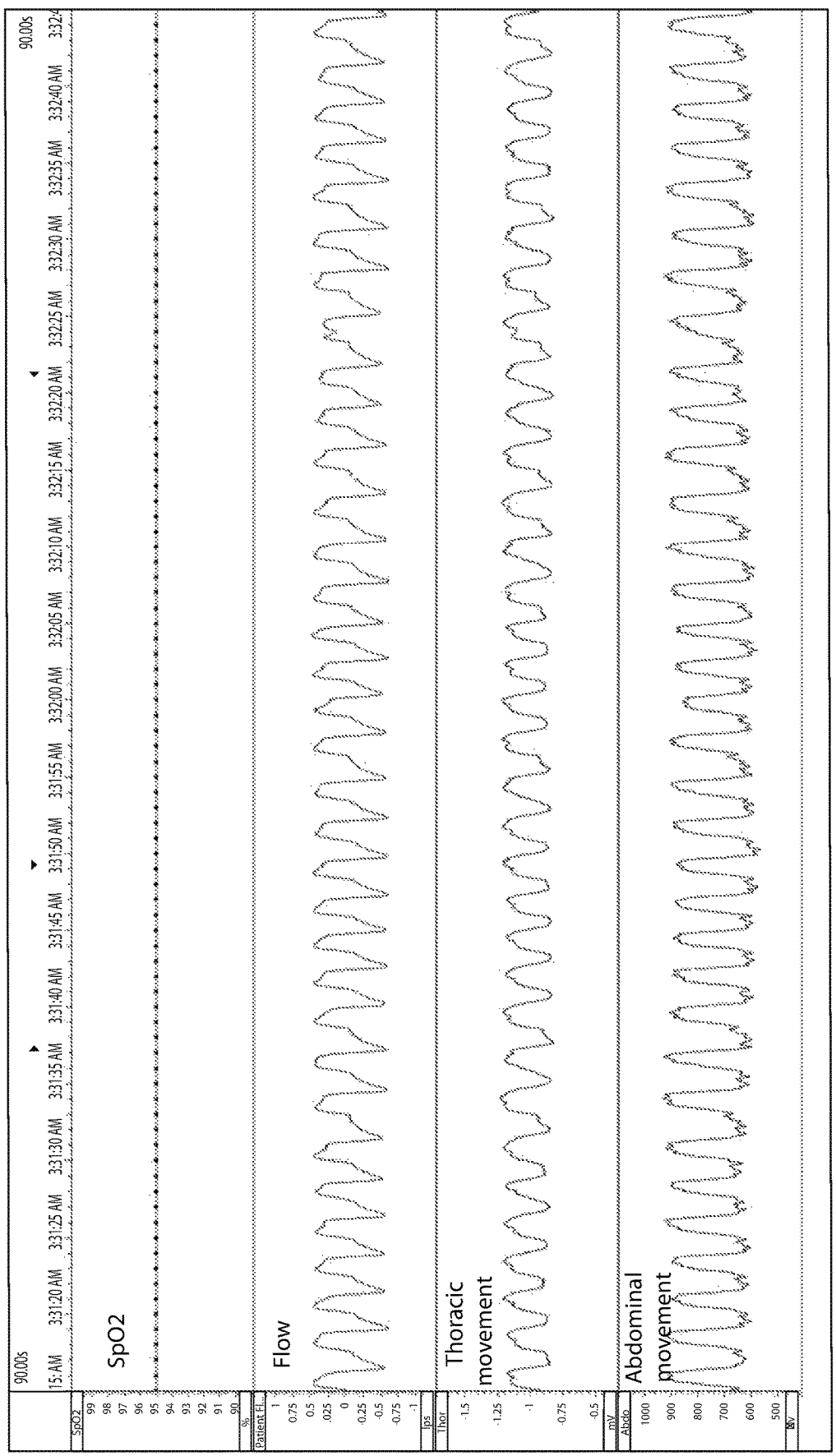
FIG. 4 shows a patient during non-REM sleep breathing normally over a period of about ninety seconds.

FIG. 4 shows a patient during non-REM sleep breathing normally over a period of about ninety seconds, with about 34 breaths, being treated with APAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 LPS in a vertical direction, and with inspiration positive. Thoracic and abdominal movement are shown in the third and fourth channels.

Figure 5:
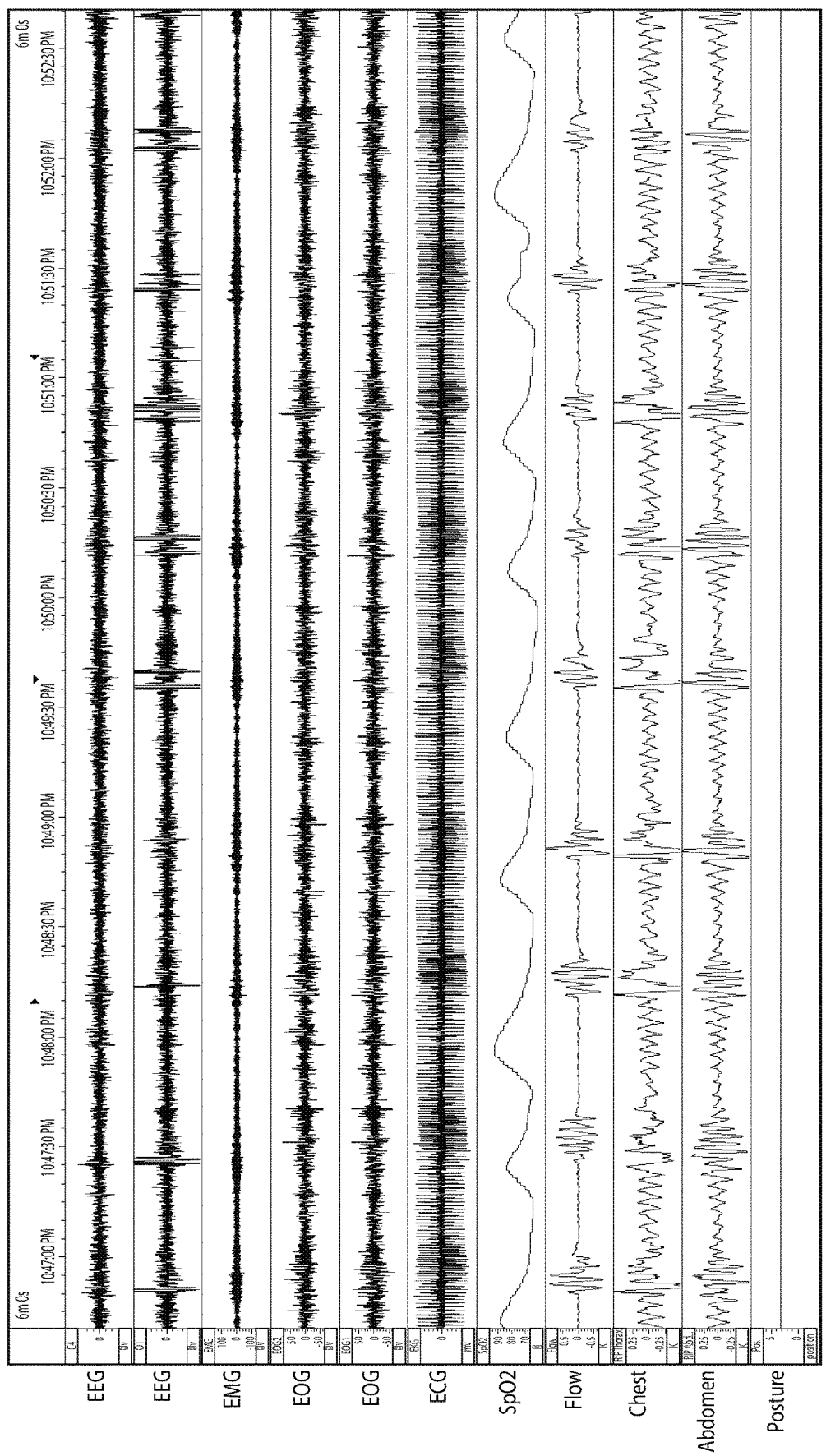
FIG. 5 shows polysomnography of a patient before treatment.

FIG. 5 shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOGs (electrooculograms). The sixth channel is an electocardiogram. The seventh channel shows pulse oximetry (SpO$_2$) with repetitive desaturations to below 70% from about 90%. The eighth channel is respiratory flow rate using a nasal cannula connected to a pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 6A:
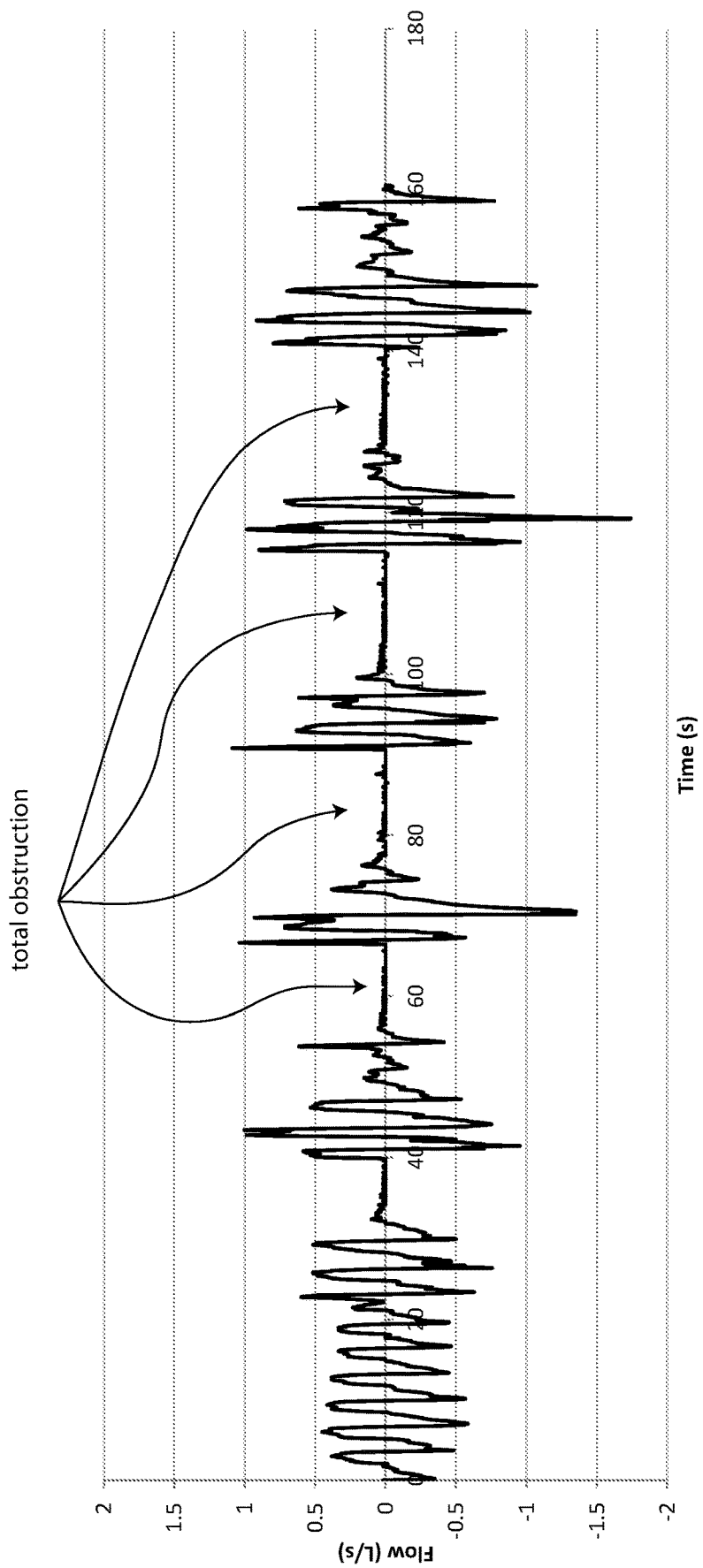
FIG. 6A shows patient flow data where the patient is experiencing a series of total obstructive apneas.

FIG. 6A shows patient flow rate data where the patient is experiencing a series of total obstructive apneas. The duration of the recording is approximately 160 seconds. Flow rates range from about +1 L/s to about −1.5 L/s. Each apnea lasts approximately 10 to 15 seconds.

Figure 6B:
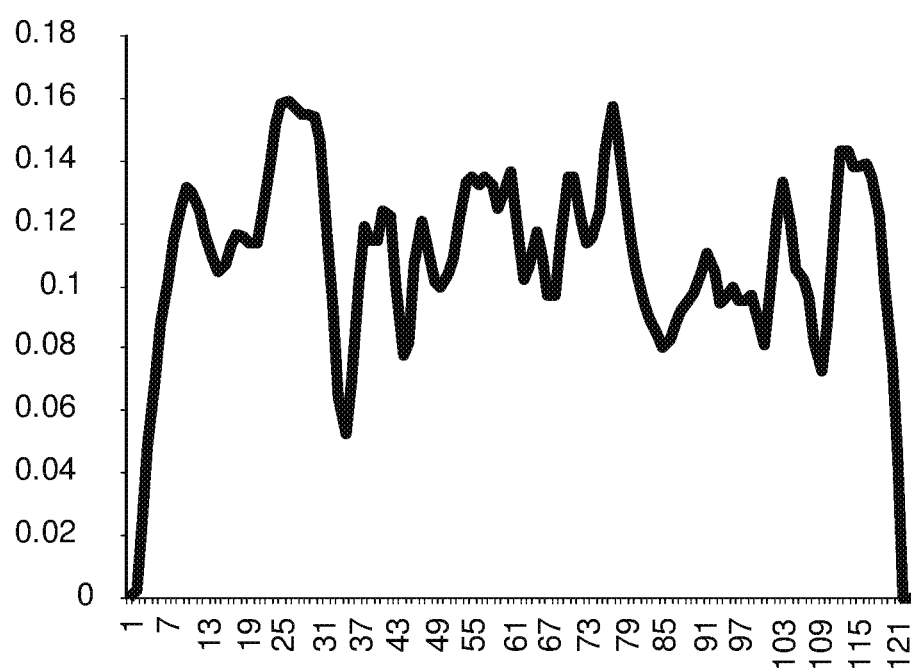
FIG. 6B shows a scaled inspiratory portion of a breath where the patient is experiencing low frequency inspiratory snore.

FIG. 6B shows a scaled inspiratory portion of a breath where the patient is experiencing low frequency inspiratory snore.

5.2 Screening/Diagnosis/Monitoring Systems and Methods

5.2.1 Screening/Diagnosis/Monitoring Systems

FIG. 7A shows a patient 1000 undergoing polysomnography. The patient 1000 is wearing an oro-nasal cannula 2050 connected to a headbox 2000 containing a pressure transducer (not shown). A polysomnography system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oronasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

FIG. 7B is a schematic representation of a system 7000 for screening, diagnosing, or monitoring SDB in accordance with one form of the present technology. The system 7000 comprises a nasal cannula 7010. The nasal cannula 7010 is a device comprising one or two open-ended projections or prongs that are configured in use to be inserted non-invasively a little way into the nares of the patient 1000. The hollow projections are in fluid communication with a Y-piece 7020 that in turn connects to a flexible conduit 7030. The conduit 7030 terminates in an adaptor 7050 configured to receive a portable computing device 7040. The adaptor 7050 may be made of inexpensive material, e.g. cardboard or plastic. FIG. 7C is an illustration of one implementation of a screening/diagnosis/monitoring system 7000 comprising an adaptor 7050. The adaptor may be configured as a cradle. The cradle may be configured with a sleeve portion 7060 to generally conform, such as with a loosely spaced gap, about a perimeter of a housing portion or end housing portion 7061 of the portable computing device. Optionally, an inner surface of the sleeve portion may engage the perimeter housing portion or end housing portion such as with an interference fit or a flexibly stretching fit. The cradle may be in the form of a generally rectangular cradle. Thus, the cradle may receive an end of a portable computing device 7040 in the form of a smartphone. The adaptor may also include a conduit 7030, which may be integrated with or be couple-able (removably coupled) to the adaptor at a channel 7051 of the cradle. In this regard, the cradle may include a channel through the cradle. The channel serves as an acoustic path from the conduit. The channel may be aligned in the cradle to permit direct alignment of the channel through the cradle with a microphone opening of the housing of the smartphone/portable computing device when the smartphone/portable computing device is inserted in the cradle. Thus, the cradle may promote isolation of the pressure/sound condition of the conduit with the microphone opening and may otherwise attenuate general ambient noise outside the cradle.

In other implementations, the adaptor 7050 may take the form of a clip that is configured to receive a portion of the end of the conduit 7030 while retaining the portable computing device 7040 such that the end of the conduit 7030 is positioned in, and may be maintained at, proximity with a microphone of the portable computing device 7040. FIG. 7D is an illustration of such an implementation of the system 7000 comprising an adaptor 7050 in the form of a clip, a portable computing device 7040 in the form of a smartphone, and a conduit 7030 (integrated or removably coupled with the adaptor). Processor control instructions stored on the portable computing device 7040 and running in a processor thereof as described below may generate an icon 7090 at a desired location on the display, taking into account the size of the clip and the location of the microphone relative to the display, so as to provide an indicator of the location on the portable computing device where the clip may be coupled to the device. Thus, when aligned with the icon 7090 displayed on a display of the smartphone example of the portable computing device 7040, the clip version of the adaptor 7050 positions the end of the conduit 7030 in proximity with a microphone of the smartphone. FIG. 7E is a side view of the clip version of the adaptor 7050 holding the end of the conduit 7030. In this regard, similarly to the channel of the cradle version of the adaptor 7050, the clip version of the adaptor 7050 may include a channel 7051, such as centrally through the clip, that provides an acoustic path from the conduit 7030 and through the clip to communicate a pressure/sound condition of the conduit 7030 in a manner that more directly aligns the outlet of the conduit 7030 to the microphone opening of the housing of the computing device 7040. The channel 7051 may have a coupling edge 7053 with an end that may engage the housing of the computing device 7040. The coupling edge 7053 may have a profile or contour (e.g., curved) to correspond with a housing of the computing device 7040 such as in a region of a microphone opening in the housing of the computing device 7040. The coupling edge 7053 may be configured to encircle or surround, at least partially or completely, the microphone opening, near the edge of the opening, of the housing of the computing device 7040 to improve isolation of the pressure condition of the channel and the microphone when the clip is engaged in its coupled and aligned position on the housing of the computing device 7040. Optionally, such a coupling edge 7053 may also be part of the cradle version of the adaptor 7050 previously described, such that it may extend from the channel 7051 inside of the cradle.

For example, the clip may include an alignment feature, such as an alignment aperture 7091 as illustrated in FIG. 7D. The alignment aperture may provide a window for visually aligning the clip with the icon 7090 displayed on the display of the portable computing device 7040. In this regard, the icon 7090 or some portion thereof may serve as a target and have a similar or corresponding shape to a window formed by the alignment aperture 7091 so that proper positioning of the clip is visually enabled by both the clip and the application running on the portable computing device 7040. As illustrated in the example of FIG. 7D, the target portion of the icon 7090 generated on the display is visible through the alignment aperture 7091 of the clip, so that the clip may be applied to the display at the icon 7090. The channel of the clip is thereby appropriately aligned to the microphone of the portable computing device 7040.

FIG. 9A is a plan view of an alternative implementation of the adaptor 7050 of FIG. 7B in the form of a clip 9000 that is configured to position the end of the conduit 7030 in proximity with a microphone of the smartphone example of the portable computing device 7040. Certain exemplary dimensions of the clip 9000 are noted in millimetres. FIG. 9B is a cross-sectional view of the clip 9000 showing the end 9010 of the conduit 7030, the channel 9051 and coupling edge 9053. Certain exemplary dimensions of the clip 9000 are noted in millimetres.

In an alternative implementation, the conduit 7030 and cannula 7010 are omitted and the adaptor 7050 takes the form of a directionally selective sound amplifier that is connected directly to the microphone of the portable computing device 7040. One example of such a directionally selective sound amplifier is generally conical in shape, tapering outward from the microphone (analogous to an old-fashioned "ear trumpet"), which acts to amplify sound originating from the direction of the axis of the cone.

Alternative implementations of the system 7000 may be applicable to disorders other than SDB that are indicated by biosounds other than breathing. In such implementations the cannula 7010 may be replaced by an interface configured to sense the particular biosound indicative of the disorder of interest. One example is the headpiece of a stethoscope that may be used to sense the sound of a heart beating. The headpiece may be coupled to the clip or cradle versions of the adaptor 7050 rather than the cannula so as to provide heartbeat sound to the microphone.

FIG. 7F is a block diagram illustrating an example of the portable computing device 7040 of the system 7000 of FIG. 7B in greater detail. The portable computing device 7040 contains a microphone 7160 which generates a signal representative of the pressure fluctuations at the diaphragm of the microphone 7160. The microphone 7160 is positioned and the conduit 7030 and adaptor 7050 are configured such that when, in use, the portable computing device 7040 is received by the adaptor 7050, the conduit 7030 acts as an acoustic waveguide conducting the pressure fluctuations in the audio frequency range (sound) at the entrance to the nares of the patient 1000 to the microphone 7160 via the adaptor 7050, while other (ambient) sources of pressure fluctuation are relatively attenuated, due to the configuration of the cradle or clip, before reaching the microphone 7160. The signal generated by the microphone 7160 is therefore substantially representative of, and only of, the nasal pressure fluctuations of the patient 1000 in the audio frequency range.

To accomplish this, the conduit 7030 may be hollow. However, such a hollow configuration is not required. Optionally, it may be solid through, or contain a sound-conducting material other than air. In addition, the microphone 7160 may have a frequency response that approximates the spectrum of human-audible sound (the audio frequency range), e.g. 10 Hz to 20 kHz, or some portion thereof. The microphone 7160 may therefore relatively attenuate any non-audio frequency components of pressure fluctuation that manage to reach the microphone 7160. Such non-audio components include components of pressure fluctuation around the breathing frequency range (0.1 to 0.5 Hz) that result from breathing itself. For these reasons, the nasal pressure fluctuation signal generated by the microphone 7160 may also be referred to as the breathing sound signal. This terminology is particularly apt when the patient 1000 is asleep as other sources of audio-range pressure fluctuation such as speech are not present. Furthermore, the prongs of the nasal cannula 7010 may be configured, e.g. with sharp edges or rough surfaces, to slightly impede the patient's respiration, so as to increase the amount of turbulence of respired air around the entrance to the nares and therefore the volume of breathing sound pressure fluctuations reaching the microphone 7160. This is a similar principle to that on which oral whistles are constructed. Alternatively, it may be desirable to have a quieter implementation, in which case the prongs may be configured to be more aerodynamic in order to reduce the turbulence of the respired air.

The microphone 7160 may include components to sample or discretise the breathing sound signal produced at the microphone's transducer. The result is a breathing sound signal in the form of a sequence of discrete samples at a sampling rate, e.g. 16 kHz.

There is a difference between the breathing sound signal generated by the microphone 7160 and a respiratory flow rate signal conventionally obtained from a nasal cannula connected to a pressure transducer. The flow rate signal produced by a pressure transducer contains a fundamental component at the patient's breathing rate, in addition to audio-range frequency components, while the breathing sound signal lacks the breathing-rate fundamental but has useful content in the audio frequency range. The breathing sound signal is therefore suitable to be generated by the microphones typically present in commercially available portable programmable computing devices such as smartphones, whose response approximates the audio frequency range.

The portable computing device 7040 also contains a processor 7110 configured to execute encoded instructions. The portable computing device 7040 also contains a non-transient computer readable memory/storage medium 7130. The memory 7130 may be the internal memory of the portable computing device 7040, such as RAM, flash memory or ROM. In some implementations, memory 7130 may also be a removable or external memory linked to portable computing device 7040, such as an SD card, server, USB flash drive or optical disc, for example. In other implementations, memory 7130 can be a combination of external and internal memory. Memory 7130 includes stored data 7140 and processor control instructions (code) 7150 adapted to, when executed, configure the processor 7110 to perform certain tasks. Stored data 7140 can include breathing sound data generated by the microphone 7160 during a screening/diagnosis/monitoring session, and other data that is provided as a component part of an application. Processor control instructions or code 7150 can also be provided as a component part of an application. The processor 7110 is adapted to read the code 7150 from the memory 7130 and execute the encoded instructions. In particular, the code 7150 may contain instructions that, when executed, configure the processor 7110 to carry out methods of processing the breathing sound signal provided by the microphone 7160. One such method may be to record the breathing sound signal for the session as data 7140 in the memory 7130. Another such method may be to analyse the recorded breathing sound data to detect SDB events such as apneas and hypopneas. One such analysis method is described in detail below. The processor 7110 may store the output(s) of such analysis methods as data 7140 in the memory 7130.

The portable computing device 7040 may also contain a communication interface 7120. The code 7150 may contain instructions configured to allow the processor 7110 to communicate with a remote computing device, e.g. a server (not shown) via the communication interface 7120. The mode of communication may be wired or wireless. In one such implementation, the processor 7110 may transmit the breathing sound recording from the data 7140 to the remote computing device via the communication interface 7120. In such an implementation, a processor of the remote computing device may be configured to analyse the received breathing sound recording to detect SDB events. In another such implementation, the processor 7110 may transmit the analysis results from the data 7140 to the remote computing device via the communication interface 7120.

Optionally, such processor control instructions (code) may be loaded as software or firmware using an appropriate data storage medium or processor-readable medium. Optionally, such processing instructions may be downloaded such as from a server over a network (e.g. an internet or the Internet) to the portable computing device such that when the instructions are executed, the portable computing device serves as a screening, diagnosing, and/or monitoring device. Thus, the server may be configured to transmit the processor control instructions (code) to the portable computing device, such as over a network, in response to requests from the portable computing device. Such a server may be configured to receive requests for downloading the processor-executable instructions from a processor-readable medium of the server to a processor-readable medium(s) of one or more portable computing device(s) over the network.

FIG. 10 is a schematic representation of a system 7000a for screening, diagnosing, or monitoring SDB in accordance with an alternative form of the present technology. The system 7000a is the same as the system 7000 of FIG. 7B, with an additional element in the acoustic path: an acoustic resonator 7070. The acoustic resonator 7070 may be placed anywhere along the conduit 7030 and is not intended to be limited by position to the illustrated position, close to the adaptor 7050. The acoustic resonator 7070 may be a Helmholtz resonator or a cavity waveguide, and is configured to modulate the breathing sound signal by concentrating the power of the signal around the resonant frequency of the resonator 7070. In one implementation, the acoustic resonator is configured such that its basic resonant frequency is around the lower end of the audio frequency range, for example 300 Hz. In some implementations, the resonant frequency of the resonator 7070 shifts away from its basic or default value as a function of pressure in the conduit 7030, which varies cyclically over the breathing cycle.

5.2.2 Screening/Diagnosis/Monitoring Methods

FIG. 7G is a flow chart illustrating a method 7200 of screening, diagnosing, or monitoring SDB according to one form of the present technology. The method 7200 may be executed by a processor 7110 of the portable computing device 7040 of the system 7000 of FIG. 7B or by a processor of a remote computing device to which the portable computing device 7040 is connected via the communication interface 7120 as described above. The method 7200 is suitable for use on the breathing sound signal generated by the microphone 7160 of the portable computing device 7040 in the system 7000.

The method 7200 may be used as a screening/diagnosis method, in which case it may applied after a session to a breathing sound signal recorded during the session and stored in the data memory 7140, or as a monitoring method, in which case may be applied during a session to a breathing sound signal generated by the microphone 7160, in or near real time. Screening typically gives a true/false result indicating whether or not a patient's SDB is severe enough to warrant further investigation, while diagnosis results in clinically actionable information.

A premise of the method 7200 considers that even normal (non-disordered) breathing creates sound due to turbulence of the respiratory airflow in the air passages, and that the instantaneous level of sound (the loudness) increases generally with the respiratory flow rate. It follows that the loudness varies in a periodic manner synchronously with the breathing cycle (see FIG. 3), and the amplitude of the loudness variation generally follows the amplitude of respiration (deep or shallow).

The first step 7210 of the method 7200 is therefore to extract an instantaneous "loudness" signal from the breathing sound signal. In one form of the present technology, this may be done by filtering (e.g., band pass filtering) the breathing sound signal to limit included frequencies to some portion of the audio frequency range, e.g. 50 Hz to 4 kHz, taking some value (e.g. the root mean square (RMS)) of the breathing sound signal within a window, e.g. of width 0.1 seconds, that slides over the breathing sound signal, e.g. at steps of 0.05 seconds for a 50% overlap. The result is a loudness signal with a sampling interval equal to the sliding window step size, e.g. 0.05 seconds.

In another implementation, step 7210 partitions the breathing sound signal into sections of short length, e.g. 0.1 seconds. The sections may be overlapping, e.g. by 50%. Step 7210 then applies a window function, e.g. a Hanning window or similar, to the samples within each section, and Fourier transforms, such as by a discrete Fourier transform or fast Fourier transform process, the samples within the windowed section. Step 7210 then sums the magnitudes of the Fourier transform values within some portion of the audio frequency range, e.g. 50 Hz to 4 kHz. The result is a loudness signal at a sampling interval equal to the section length multiplied by one minus the overlap fraction, e.g. 0.05 seconds.

FIG. 8A shows a graph 8000 containing two traces, the upper trace 8010 representing the loudness of a recorded breathing sound signal over a period of five breaths, and the lower trace 8020 representing respiratory flow rate over the same period of five breaths. The loudness trace 8010 is scaled to make the loudness trace 8010 approximately match the respiratory flow rate trace 8020 in amplitude. It may be seen that the loudness trace 8010 contains two peaks for each breath discernible in the respiratory flow rate trace 8020. One peak, e.g. 8015, is coincident with the inspiratory portion, e.g. 8030, of the breath, and one peak, e.g. 8025, is coincident with the expiratory portion, e.g. 8040, of the breath. The two peaks 8015 and 8025 are separated by a silent trough coincident with the transition between inspiration and expiration. The loudness 8010 resembles a rectified version of the respiratory flow rate trace 8020, since loudness generally increases with the magnitude of the respiratory flow rate, regardless of the sign of the respiratory flow rate.

FIG. 8B contains a graph 8050 also containing two traces, the upper trace 8060 representing the loudness of a recorded breathing sound signal, and the lower trace 8070 representing respiratory flow rate. It may be seen that the amplitude of variation of the loudness trace 8060 roughly matches the amplitude of variation of the respiratory flow rate trace 8070.

FIG. 8C shows a graph 8100 also containing two traces, the upper trace 8110 representing the loudness of a recorded breathing sound signal, and the lower trace 8120 representing respiratory flow rate. It may be seen that the amplitude of variation of the loudness trace 8110 roughly matches the amplitude of variation of the respiratory flow rate trace 8120. In particular, during an apnea 8130, the loudness trace 8110 falls to an insignificant level.

Continuing with the method of FIG. 7G, step 7215 of the method 7200 may be applied to normalise the loudness signal to the range [0, 1]. In one implementation, step 7215 subtracts from each loudness sample the minimum loudness value in a window surrounding the sample. The window may be chosen to be long enough to contain some breathing even with severe apneas, e.g. a 2-minute window. Step 7215 then divides the loudness signal by the 99th percentile value within the centred window.

Optionally, step 7215 may filter, such as with a bandpass filter, the normalised loudness signal to remove frequencies outside the normal breathing frequency range for adults, e.g. below 10 breaths per minute and above 60 breaths per minute (approximately twice the usual upper limit of 30 breaths per minute, to take into account the fact that the loudness signal is similar to a rectified version of the respiratory flow rate). This permits an upper frequency of the bandpass range to remain in the filtered loudness signal where the upper frequency is two times an upper frequency limit of a human breathing frequency range.

FIGS. 8B and 8C indicate that conventional apnea and hypopnea detection methods, as usually applied to a respiratory flow rate signal, may be applied to the loudness signal to detect apneas and hypopneas with reasonable accuracy. The steps 7220 and 7230 of the method 7200 therefore detect apneas and hypopneas respectively from the loudness signal. The steps 7220 and 7230 are independent and may be performed in sequence or in parallel, as illustrated in FIG. 7G. Conventional apnea/hypopnea detection methods typically involve comparing a short-term averaged value of a respiration-related signal (in the present technology, the loudness signal) with a typical value from the same signal over a longer term. If the former falls to some fraction of the latter (e.g. 10% for an apnea, 30% for a hypopnea) for a minimum duration, an apnea/hypopnea is detected. One implementation of step 7220 therefore detects apneas as periods where the normalised loudness signal falls below 0.1 for at least 10 seconds. Likewise, one implementation of step 7230 detects hypopneas as periods where the normalised loudness signal falls below 0.3 for at least 10 seconds.

The method 7200 then at step 7240 computes a metric of severity of SDB experienced by the patient 1000 during the session from the detected apneas and hypopneas. In one implementation, step 7240 computes and returns an apnea-hypopnea index (AHI) by dividing the number of detected apneas and hypopneas by the length of the session. The AHI is a conventional indicator of the degree of severity of a patient's SDB.

At step 7250, the method 7200 generates an output based on the SDB severity metric computed at step 7240 and/or the events detected at steps 7220 and 7230. The generated output may be conveyed to a user via an output device of the computing device 7040, e.g. a display. In one implementation, suitable for a diagnosis/monitoring application, the output is simply the SDB severity metric. In another implementation, suitable for a screening application, step 7250 compares the SDB severity metric with a severity threshold and returns, for example, a Boolean value of True if the SDB severity metric exceeds the severity threshold, indicating the patient's SDB is sufficiently severe to warrant more detailed investigation, or False, indicating the opposite. In the case where the SDB severity metric is an AHI, a typical severity threshold is 15.

In some implementations of step 7250, the computing device 7040 may be configured to, on request by a user, such as by activating a playback option of a graphic user interface (button/menu option etc.) that is generated by the computing device 7040, play back 'interesting' portions of the recorded loudness signal, e.g. those containing detected apneas, optionally synchronised with some kind of visual representation of the sound. This playback output can act as a strong indicator to the user that all is not well with their breathing during sleep and that they need to seek medical advice. The playback may, for example, provide a visual display of the recorded loudness signal, and may include a time indication of breathing absence(s) associated with apnea, on a display of the computing device 7040. The playback option may also or alternatively provide an audible version of the recorded loudness signal via a speaker of the computing device 7040.

The method 7200 may include more sophisticated analysis of the normalised loudness signal. Such analysis may be enabled by "de-rectifying" the loudness signal, i.e. identifying which peaks of the loudness signal correspond to inspiratory portions and which peaks correspond to expiratory portions of a breathing cycle, and assigning a negative value to the expiratory portions. Step 7215 may carry out "de-rectification" in addition to normalisation and band-pass filtering. Criteria that may be evaluated to implement such a process in a processor so as to distinguish inspiratory peaks from expiratory peaks may include:

Differing periods between peaks—e.g. during sleep, inspiration will generally be shorter in duration than expiration. For example, such a process may determine a duration of a period between two successively detected peak values of the loudness signal and evaluate the duration by comparing the duration to a threshold. The threshold may be a predetermined threshold. The threshold may be a threshold defined by durations of other determined periods between successive peaks of the signal (e.g., an average of a plurality of determined periods or even a duration of a neighbouring period such as a preceding or following period). If the period is so determined to be short with the threshold comparison (e.g., the duration is less than the threshold), the initial peak of the period may be taken as an inspiratory peak and/or the latter peak of the period may be taken as an expiratory peak.

The signal shape—expiratory peaks may be more exponentially decaying in shape than inspiratory peaks. For example, such a process may evaluate the curve of the loudness signal following a detected peak by applying any curve fitting techniques to detect which of two successive peaks fits more closely to an exponentially decaying shape.

Frequency content, e.g. spectral entropy (see below)—during inspiration, the airway is generally more constricted than during expiration, giving rise to different spectral characteristics. For example, such a process may evaluate spectral entropy from a section of the signal associated with a peak. A value of the spectral entropy may then be compared to a threshold for determining whether it corresponds with inspiration or expiration. The threshold value may be determined as a fraction value referenced to the peak values in periodic fluctuation of the spectral entropy, where the period of interest is within the range of the expected breath periods of the subject. In another example, the spectral entropy from each of two successive sections of the signal having a peak may be compared to determine which is expiration and which is inspiration.

The result of such "de-rectification" is an approximation to the respiratory flow rate signal. More generally, there exists a (non-linear) transfer function from respiratory flow rate to loudness of breathing sound. The process of inverting this transfer function, and thereby estimating respiratory flow rate from breathing sound loudness, is known as phonospirometry.

Once the inspiratory and expiratory peaks in the loudness signal have been identified, the analysis method 7200 may include detecting additional SDB events such as snoring and flow limitation. Features that may be used to detect snore in the loudness signal (such as the de-rectified loudness signal), or the breathing sound signal, may include:

Inspiratory loudness peaks of snore breaths may be flatter than those of breaths without snore. For example, such a process may determine and evaluate a measure of inspiratory flatness (or absence of roundness) of peaks of an inspiratory section of the loudness signal. The measure(s) may be evaluated such as by comparison of the measure(s) to a threshold(s) to identify the section as including snoring or not including snoring.

A high number of peaks in the Fourier spectrum of the loudness signal within the range of snore sounds (for example 20 to 1000 Hz) where the peaks are approximately evenly spaced in the spectrum. For example, such a process may apply a fast Fourier transform to a section of the loudness signal and may evaluate the uniformity of the distances between detected peaks of the resulting spectrum within the range of snore sounds by analysing the variance in the distance between peaks, or by calculating the spectrum of the spectrum and identifying sections of that signal with an increase in energy that falls within the expected range of periods of fundamental snore period of snore signals as predicted by analysis of a snoring population.

Rate of change of the loudness signal may start low and increase as a critical flow rate is reached to start oscillation of the airway (snore). This can produce an inflection point of increasing rate of change (negative-going zero crossing in the second derivative) in the loudness signal toward the beginning of inspiration. For example, such a process may determine the second derivative of the loudness signal of an early portion of an inspiratory section of the signal. The process may then detect occurrence of a negative-going zero crossing in the second derivative signal. The process may then identify the section of the loudness signal as one that includes a snoring event from the detection of the occurrence.

An increase in the deterministic component of the breathing sound signal may be indicative of acoustic noise sources being influenced by airway mechanics (such as in snore). Parameters reflecting this may include kurtosis (a measure of how Gaussian the signal is), Spectral Entropy (a measure of "whiteness", i.e. how random or disordered the signal is). For example, a more random (higher kurtosis or entropy) signal would be expected to be a result of turbulent noise sources, while a more deterministic or orderly signal (lower kurtosis or entropy) might indicate more interaction with airway mechanics, such as during snoring. For example, such a process may determine a measure(s) of kurtosis and/or Spectral Entropy of the breathing sound signal. The measure(s) may then be compared to one or more thresholds, such as a predetermined threshold(s) or a measure(s) of kurtosis and/or Spectral Entropy determined from other portions of the breathing sound signal. An event of snore may then be determined based on the threshold comparison(s).

In addition, significant gaps in the entropy/kurtosis time series of the breathing sound signal may be used to detect apneas and hypopneas. For example, such a process may determine a time series of measure(s) of kurtosis and/or Spectral Entropy of the breathing sound signal, for example, by calculating the kurtosis and/or Spectral Entropy for a sliding window along the signal. The time series values may then be compared to one or more thresholds, such as a predetermined threshold(s) or a measure(s) of kurtosis and/or Spectral Entropy determined from other portions of the breathing sound signal. An apnea or hypopnea may then be determined based on the threshold comparison(s), such as when the time series values fall below the threshold for longer than a minimum duration.

Features that could be used to detect flow limitation in the de-rectified loudness signal may include:

Any of the above described features/processes associated with snore, which when providing a positive snore indication, may be taken as an indication of an increase in the probability of flow limitation being present.

An increasing ratio of inspiratory peak loudness to expiratory peak loudness can be indicative of an increased probability of flow limitation. For example, such a process may determine a series of ratios where each ratio is a ratio of inspiratory peak loudness $I_{PL}$ of an inspiratory portion of the loudness signal and an expiratory peak loudness $E_{PL}$ of a related expiratory portion (e.g., $I_{PL}/E_{PL}$). Such a series of ratios may be two or more ratios such as in a continuous signal of ratios computed from the loudness signal. The ratio signal may then be evaluated to detect an increase in the ratio signal, such as by evaluation of a derivative of the ratio signal. Alternatively, two such ratios may be compared to detect a difference. A significant difference, such as a large enough increase as determined with a threshold, may then be taken as an indication of flow limitation.

An increase in the fundamental frequency of any detected snoring can be indicative of flow limitation. For example, such a process may determine the fundamental frequency (e.g., lowest frequency taken from a fast Fourier transform) from sequential sections of the loudness signal. Such a series of fundamental frequencies may be considered a signal of fundamental frequencies. The signal may then be evaluated to detect one or more increases in the signal (e.g., with a derivative signal determined from the fundamental frequency signal) that may be taken as an indication of flow limitation. Alternatively, two determined fundamental frequencies from different sections of the loudness signal may be compared to detect a difference. A significant difference, such as a large enough increase as determined with a threshold, may then be taken as an indication of flow limitation. Optionally, the rate of change of the of the fundamental frequency or any harmonics may be evaluated as an indicator of either the onset of flow limitation or the recovery from flow limitation. Optionally, such analysis may be taken as an indicator of the character of the disease that the flow limitation is a part of.

The detection of SDB events such as snoring and flow limitation enable alternative severity metrics such as a snoring index or a flow limitation index to be computed at step 7240 and output at step 7250 in similar fashion to the AHI described above.

Another application of a de-rectified loudness signal is sleep stage inference. A time series of inferred sleep stages, known as a hypnogram, may be obtained from a respiratory flow rate signal for example using the method of PCT Publication WO 2017/132726, the entire contents of which are herein incorporated by reference. Such a methodology for sleep stage inference described in this publication may be applied to the example loudness signal(s) described herein.

In some implementations, the method 7200 may further include submitting a questionnaire to the patient before or after the signal processing steps. The generated output from step 7250 may then take into account the answers supplied by the patient to the questionnaire questions, such as when the answers are input to the portable computing device in response to an automated query, as well as the computed severity metric. One example of such a questionnaire is the STOP-BANG questionnaire used to screen for sleeping disorders. A further source of data that may be taken into account by step 7250 is personal details of the patient, e.g. age, bodyweight, and gender, which may also be input to the portable computing device in response to an automated query.

A measure of quality of the loudness signal may be computed as part of step 7215 of the method 7200. One example of such a quality measure is a binary measure of "high quality" or "low quality". A loudness signal being marked as "low quality" may cause the method 7200 to halt before steps 7220 and 7230 are executed, or otherwise skip steps 7220 and 7230. In one implementation of calculating a binary measure of quality, a loudness signal is marked as "low quality" if it does not have most of its power in the human breathing frequency range. This may be quantified by subtracting the band-pass filtered (normalised) loudness signal of step 7215 from the raw (normalised) loudness signal to obtain the out-of-range power, and comparing with the power of the band-pass filtered loudness signal. Optionally, such a measure of quality using signal subtraction may be applied to discrete portions of the loudness signal.

Other quality measures may be calculated for portions of the loudness signal. In one example, portions of the loudness signal may be evaluated in relation to an expected profile (shape) of one or more breaths. In such an example, if a similarity between the loudness signal and the expected profile of one or more breaths is low, the loudness signal portion may be marked as "low quality" and discarded. Otherwise, the loudness signal portion may be marked as suitable (high quality). In some versions, the similarity may be computed by correlation, such by determining a cross-correlation, of the loudness signal portion with the expected profile of a breath, or by comparing a measure of variability (e.g., standard deviation and/or variance, etc.) of the loudness signal portion with one or more threshold(s).

An alternative method may be suitable for analysis of the breathing sound signal such as when the breathing signal is generated by the microphone 7160 of the portable computing device 7040 shown in the alternative system 7000*a* of FIG. 10. The alternative analysis method may be the same as the method 7200 of FIG. 7G, except that the step 7210 that extracts the loudness signal calculates the power in the resonant frequency range of the resonator 7070 of a window that slides along the breathing sound signal. Non-breathing sounds are more likely to fall outside this range as they have not passed through the resonator 7070, and so contribute less to the loudness signal than genuine breathing sounds.

In a further alternative method suitable for analysis of the breathing sound signal generated by the microphone 7160 of the portable computing device 7040 in the alternative system 7000*a* of FIG. 10, the step 7210 extracts a loudness signal by determining a signal that represents the frequency modulation that occurs around the basic resonant frequency of the resonator 7070. For example, such a representative signal may be determined with frequency demodulation (e.g., using a demodulator or processing methodology to achieve demodulation) so as to extract the variation of the the resonant frequency. This approach to loudness signal extraction is suitable for implementations of the resonator 7070 in which the resonant frequency of the resonator 7070 shifts away from its basic or default value as a function of nasal pressure, which varies cyclically over the breathing cycle in the same manner as respiratory flow rate.

A further alternative analysis method does not resemble the method 7200, but rather analyses the breathing sound signal using a generic acoustic model of the airway. Such an analysis of the breathing sound signal of a patient may give parameters of the airway model for a given patient at a given time, such as diameter and collapsibility of the airway. These parameters in turn may be used to screen, diagnose, or monitor a patient's SDB. The analysis may also be carried out on the passively recorded breathing sound signal emitted by the patient 1000, or on acoustic (e.g. ultrasonic) excitations such as pulses and chirps transmitted from a speaker of the portable computing device 7040 down the conduit 7030 and reflected back from the airway of the patient 1000 to the microphone 7160.

FIG. 7H is a flow chart illustrating a method 7300 of screening, diagnosing, or monitoring SDB according to another form of the present technology. The method 7300 may be executed by a processor 7110 of the portable computing device 7040 of the system 7000 of FIG. 7B or by a processor of a remote computing device to which the portable computing device 7040 is connected via the communication interface 7120 as described above. The method 7300 is suitable for use on the breathing sound signal generated by the microphone of the portable computing device 7040 in the system 7000.

The method 7300 is similar to the method 7200 of FIG. 7G, with the steps 7310, 7315, and 7350 being the same as their counterpart steps 7210, 7215, and 7250 in the method 7200. Step 7325 de-rectifies the loudness signal as described above. Step 7330 detects periods of Cheyne-Stokes respiration (CSR) from the normalised, de-rectified loudness signal. Conventional methods of detecting CSR periods in a respiratory flow rate signal may be used for step 7330, treating the de-rectified loudness signal as a respiratory flow rate signal. Steps 7340 computes a severity metric based on the detected CSR periods from step 7330. In one example, step 7340 adds the durations of all detected CSR periods and divides by the length of the session to obtain a fractional or percentage value. Such a fractional or percentage value may then serve as a CSR severity indicator based on the loudness signal and may be output by a processor of the remote computing device of the portable computing device.

A further alternative to the system 7000 of FIG. 7B comprises one or more additional sensors, each configured to generate a corresponding signal that may be processed along with the breathing sound signal by a variant of the method 7200 to improve the screening/diagnosis/monitoring performance. Examples of additional sensors include: a photoplethysmograph (PPG) configured to generate a signal representing oxygen saturation; an electrocardiogram configured to generate a signal representing the electrical activity if the heart; and an accelerometer configured to generate signals representing acceleration of the sensor in respective axes.

5.3 Glossary

For the purposes of the present technology disclosure, in certain forms of the present technology, one or more of the following definitions may apply. In other forms of the present technology, alternative definitions may apply.

5.3.1 General

Air: In certain forms of the present technology, air may be taken to mean atmospheric air, and in other forms of the present technology air may be taken to mean some other combination of breathable gases, e.g. atmospheric air enriched with oxygen.

Continuous Positive Airway Pressure (CPAP) therapy: Respiratory pressure therapy in which the pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Respiratory Pressure Therapy (RPT): The application of a supply of air to an entrance to the airways at a treatment pressure that is typically positive with respect to atmosphere.

5.3.2 Aspects of the Respiratory Cycle

Apnea: Preferably, apnea will be said to have occurred when flow falls below a predetermined threshold rate for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Apnea-Hypopnea Index (AHI): The number of apnea or hypopneas undergone by a patient, on average, per hour. AHI is a generally accepted measure of the severity of a patient's OSA.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: The state of affairs in a patient's respiration whereby an increase in effort by the patient does not give rise to a corresponding increase in flow. Where flow limitation occurs during an inspiratory portion of the breathing cycle it may be described as inspiratory flow limitation (IFL). Where flow limitation occurs during an expiratory portion of the breathing cycle it may be described as expiratory flow limitation (EFL).

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of unintentional leak from a patient interface system. Respiratory flow rate, Qr, is the flow rate of air that is received into the patient's respiratory system.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

5.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.4 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.5 Reference Signs List

| | |
|---|---|
| patient | 1000 |
| bed partner | 1100 |
| headbox | 2000 |
| ground electrode | 2010 |
| EOG electrode | 2015 |
| EEG electrode | 2020 |
| ECG electrode | 2025 |
| submental EMG electrode | 2030 |
| snore sensor | 2035 |
| respiratory effort sensor | 2040 |
| respiratory effort sensor | 2045 |
| oro-nasal cannula | 2050 |
| pulse oximeter | 2055 |
| body position sensor | 2060 |
| patient interface | 3000 |

-continued

| | |
|---|---|
| RPT device | 4000 |
| air circuit | 4170 |
| humidifier | 5000 |
| screening/diagnosis/monitoring system | 7000 |
| screening/diagnosis/monitoring system | 7000a |
| nasal cannula | 7010 |
| Y-piece | 7020 |
| conduit | 7030 |
| computing device | 7040 |
| adaptor | 7050 |
| channel | 7051 |
| coupling edge | 7053 |
| sleeve portion | 7060 |
| end housing portion | 7061 |
| acoustic resonator | 7070 |
| icon | 7090 |
| alignment aperture | 7091 |
| processor | 7110 |
| communication interface | 7120 |
| memory | 7130 |
| data | 7140 |
| code | 7150 |
| microphone | 7160 |
| method | 7200 |
| step | 7210 |
| step | 7215 |
| step | 7220 |
| step | 7230 |
| step | 7240 |
| step | 7250 |
| graph | 8000 |
| loudness | 8010 |
| peak | 8015 |
| respiratory flow rate trace | 8020 |
| peak | 8025 |
| inspiratory portion | 8030 |
| expiratory portion | 8040 |
| graph | 8050 |
| loudness trace | 8060 |
| respiratory flow rate trace | 8070 |
| graph | 8100 |
| loudness trace | 8110 |
| respiratory flow rate trace | 8120 |
| apnea | 8130 |
| clip | 9000 |
| end | 9010 |
| channel | 9051 |
| coupling edge | 9053 |

The invention claimed is:

1. An apparatus comprising:
a nasal cannula;
a conduit connected to the nasal cannula at a first end; and
an adaptor having a first end portion configured for a second end of the conduit, the adaptor having a second end portion configured to removably receive and retain, within the adaptor, at least a portion of an end of a portable computing device, the adaptor configured to align the second end of the conduit with a microphone opening of the portable computing device, wherein the adaptor is a clip.

2. The apparatus of claim 1, wherein the nasal cannula comprises one or two projections that are configured in use to be inserted non-invasively a little way into respective nares of a patient.

3. The apparatus of claim 2, wherein at least one of the one or two projections is configured to partially impede the patient's respiration.

4. The apparatus of claim 1, further comprising an acoustic resonator in the conduit.

5. The apparatus of claim 1 wherein the adaptor is configured with a channel to provide an acoustic path through the adaptor to the microphone opening of the portable computing device.

6. The apparatus of claim 1, wherein a channel of the adaptor is configured for direct alignment with the microphone opening of the portable computing device, when the adaptor is applied to the housing of the portable computing device.

7. The apparatus of claim 1, wherein the adaptor comprises a coupling edge configured to at least partially surround the microphone opening of the portable computing device.

8. A system for screening, diagnosing, or monitoring sleep disordered breathing (SDB) of a patient, the system comprising:
a nasal cannula;
a conduit connected to the nasal cannula at a first end;
an adaptor having a first end portion configured to receive a second end of the conduit, the adaptor having a second end portion configured to removably receive and retain, within the adaptor, at least a portion of an end of a portable computing device, the adaptor configured to align the second end of the conduit with a microphone opening of the portable computing device, wherein a microphone is configured to generate a breathing sound signal of the patient when the nasal cannula is mounted to a patient; and
a processor configured to compute a metric of severity of the patient's SDB from the breathing sound signal,
wherein the adaptor is a clip.

9. The system of claim 8, wherein the processor is a processor of the portable computing device.

10. The system of claim 8, wherein the processor is a processor of a remote computing device with which the portable computing device is in communication.

11. The system of claim 8, wherein the processor is further configured to generate a clip location indicator on a display coupled to the processor, wherein the clip location indicator indicates a location on the display where attachment of a clip permits alignment between a channel of the clip and the microphone.

12. The system of claim 8, wherein the adaptor is configured with a channel to provide an acoustic path through the adaptor to the microphone opening of the portable computing device.

13. The system of claim 8, wherein a channel of the adaptor is configured for direct alignment with the microphone opening of the portable computing device, when the adaptor is applied to the housing of the portable computing device.

14. The system of claim 8, wherein the adaptor comprises a coupling edge configured to at least partially surround the microphone opening of the portable computing device.

15. The system of claim 8, further comprising an acoustic resonator located in the conduit.

16. An apparatus comprising:
a nasal cannula;
a conduit connected to the nasal cannula at a first end; and
an adaptor having a first end portion configured to removably receive a second end of the conduit, the adaptor having a second end portion configured to removably receive and retain at least a portion of an end of a portable computing device, the adaptor configured to position the second end of the conduit in proximity with a microphone of the portable computing device, wherein the adaptor is a clip.

* * * * *